US005981575A

United States Patent [19]
Kuhajda et al.

[11] Patent Number: 5,981,575
[45] Date of Patent: Nov. 9, 1999

[54] INHIBITION OF FATTY ACID SYNTHASE AS A MEANS TO REDUCE ADIPOCYTE MASS

[75] Inventors: Francis P. Kuhajda, Lutherville; Gary R. Pasternack, Baltimore; Craig A. Townsend, Baltimore; Neelakandha S. Mani, Baltimore, all of Md.

[73] Assignee: Johns Hopkins University, The, Baltimore, Md.

[21] Appl. No.: 09/000,157

[22] PCT Filed: Nov. 15, 1996

[86] PCT No.: PCT/US96/17678

§ 371 Date: Jan. 27, 1998

§ 102(e) Date: Jan. 27, 1998

[87] PCT Pub. No.: WO97/18806

PCT Pub. Date: May 29, 1997

[51] Int. Cl.$^6$ ..................................................... A01K 31/04
[52] U.S. Cl. ................................................................ 514/473
[58] Field of Search .............................................. 514/473

[56] References Cited

U.S. PATENT DOCUMENTS

| | | |
|---|---|---|
| 3,535,309 | 10/1970 | Hata et al. . |
| 3,630,846 | 12/1971 | Hata et al. . |
| 3,897,428 | 7/1975 | Omura et al. . |
| 3,909,361 | 9/1975 | Hata et al. . |
| 4,000,164 | 12/1976 | Parker . |
| 4,011,334 | 3/1977 | Parker . |
| 4,032,647 | 6/1977 | Parker . |
| 4,110,351 | 8/1978 | Parker . |
| 4,146,623 | 3/1979 | Parker . |
| 4,328,246 | 5/1982 | Gold . |
| 4,602,099 | 7/1986 | Parker . |
| 4,738,984 | 4/1988 | Parker . |
| 4,789,630 | 12/1988 | Bloch et al. . |
| 4,968,494 | 11/1990 | Claremon et al. . |
| 5,032,611 | 7/1991 | Taguchi et al. . |
| 5,143,907 | 9/1992 | Spielvogel . |
| 5,185,149 | 2/1993 | Baldwin et al. . |
| 5,188,830 | 2/1993 | Atkinson et al. . |
| 5,190,969 | 3/1993 | Blumenstein et al. . |
| 5,246,960 | 9/1993 | Barbier et al. . |
| 5,614,551 | 3/1997 | Dick et al. . |
| 5,759,836 | 6/1998 | Kuhajda et al. ........................ 435/193 |

FOREIGN PATENT DOCUMENTS

| | | |
|---|---|---|
| 0 246 734 | 11/1987 | European Pat. Off. . |
| 0 374 886 | 6/1990 | European Pat. Off. . |
| 252 616 | 12/1987 | Germany . |
| 59-225115 | 12/1984 | Japan . |
| 60-058917 | 4/1985 | Japan . |
| 1-132542 | 5/1989 | Japan . |
| 2-113850 | 4/1990 | Japan . |
| 2-247125 | 10/1990 | Japan . |
| WO 93/12240 | 6/1993 | WIPO . |
| WO 93/12756 | 7/1993 | WIPO . |

OTHER PUBLICATIONS

Bacchi, et al., "Effects of Some Antitumor Agents on Growth and Glycolytic Enzymes of the Flagellate Crithidia," *J. Bacteriol.*, 98:23–28 (1969).

Furnica, et al., "Mecanismes Biochimiques Impliques Dans La Sensibilisation Des Organismes Vivants Par Des Agents Chimiques A L'Action Des Radiations et Des Cytostatiques," *Rev. Roum. Biochim.*, 8:117–122 (1971).

Ōmura, et al., "Relationship Between the Structures of Fatty Acid Amide Derivatives and Their Antimicrobial Activities," *Antimicrobial Agents and Chemotherapy*, 6:207–215 (1974).

Ōmura, Satoshi, "The Antibiotic Cerulenin, a Novel Tool for Biochemistry as an Inhibitor of Fatty Acid Synthesis," *Bacteriological Reviews*, 40:681–697 (1976).

Altenbern, Robert A., "Cerulenin–Inhibited Cells of *Staphylococcus aureus* Resume Growth When Supplemented with Either a Saturated or an Unsaturated Fatty Acid," *Antimicrobial Agents and Chemotherapy*, 11:574–576 (1977).

Altenbern, Robert A., "Extreme Sensitivity of Staphylococcal Enterotoxin B and C Production to Inhibition by Cerulenin," *Antimicrobial Agents and Chemotherapy*, 11:906–908 (1977).

Partida, et al., "Comparative Effects of Diphenylglioxal and its Superoxide on Experimental Tumors," *Arch. de Farmacol. y Toxicol.*, III:231–240 (1977).

Chen, et al., "The Cerulenin–Induced Formation of 1–Acyl–Lysophosphatidyl Glycerol in *Bacillus megaterium*," *Biochem. Biophys. Res. Comm.*, 80:126–132 (1978).

Carson, et al., "Effect of Cerulenin on *Streptococcus faecalis* Macromolecular Synthesis and Cell Division," *J. Bacteriol.*, 133:472–476 (1978).

(List continued on next page.)

Primary Examiner—James H. Reamer
Attorney, Agent, or Firm—Baker & Botts, LLP

[57] ABSTRACT

Weight loss was noted in nude mice treated with cerulenin, a non-competitive inhibitor of FAS. Sustained reduction of adipocyte mass in humans without toxicity would significantly impact disease prevention worldwide. Aside from psychological and self-esteem improvement, weight loss via reduction of adipocyte mass may: (1) ameliorate hyperglycemia associated with non-insulin-dependent diabetes mellitus thereby reducing diabetic complications such as arterial disease, blindness, cataracts, etc., (2) reduce hypertension, (3) reduce risk of coronary artery vascular disease and stroke, and (4) reduce the risk of other complications of massive obesity such as osteoarthritis, surgical complications, etc. There is also potential use in livestock and poultry to reduce the saturated fat content of meat products. Therefore FAS inhibitors are disclosed herein as novel agents for weight reduction. A family of compounds (γ-substituted-α-methylene-β-carboxy-γ-butyrolactones) whose synthesis was based on the cerulenin motif is shown herein to inhibit fatty acid synthesis, inhibit growth in certain susceptible tumor cells, and induce weight loss.

19 Claims, 9 Drawing Sheets

OTHER PUBLICATIONS

Caulfield, et al., "Export of Extracellular Levansucrase by *Bacillus subtilis*: Inhibition by Cerulenin and Quinacrine," *J. Bacteriol.*, 138:345–351 (1979).

Leung, et al., "*Streptococcus mutans* Dextransucrase: Effect of Cerulenin on Lipid Synthesis and Enzyme Production," *Infection and Immunity*, 28:846–852 (1980).

Smith, et al., "Thioesterase II, a New Marker Enzyme for Human Cells of Breast Epithelial Origin," *JNCI*, 73:323–329 (1981).

Carson, et al., "Effect of Cerulenin on Cellular Autolytic Activity and Lipid Metabolism During Inhibition of Protein Synthesis of *Streptococcus faecalis*," *J. Bacteriol.*, 146:590–604 (1981).

Bocquet–Pages, et al., "Lipid–Synthesis–Dependent Biosynthesis (or Assembly) of Major Outer–Membrane Proteins of *Escherichia coli*," *Eur. J. Biochem.*, 118:105–111 (1981).

Ōmura, Satoshi, Chapter 39 "Cerulenin" in *Methods in Enzymology*, 72:520–532 (1981).

Thompson, et al., "Purification and Properties Of Fatty Acid Synthetase From A Human Breast Line," *Biochim. Biophys. Acta*, 662:125–130 (1981).

Ahmad, et al., "Studies on Acetyl–CoA Carboxylase and Fatty Acid Synthase from Rat Mammary Gland and Mammary Tumors," *Biochem. J.*, 208:443–452 (1982).

Clements, et al., "Irreversible Inhibition of Fatty Acid Synthase from Rat Mammary Gland with S–(4–bromo–2,3–dioxobutyl)–CoA," *Biochem. J.*, 207:291–296 (1982).

Thompson, et al., "Lack of Coordinated Regulation Of Lipogenic Enzymes In A Human Breast Cell Line SKBr3," *Biochim. Biophys. Acta*, 712:217–220 (1982).

Mäntsälä, et al., "Secretion of β–lactamase by *Escherichia coli* in vivo and in vitro: Effect of Cerulenin," *Antonie van Leeuwenhoek*, 48:353–364 (1982).

Hayashi, et al., "Mechanism of Action of the Antibiotic Thiolactomycin Inhibition of Fatty Acid Synthesis of *Excherichia coli*," *Biochem. Biophys. Res. Comm.*, 115:1108–1113 (1983).

Spiegelman, et al., "Fibronectin Modulation of Cell Shape and Lipogenic Gene Expression in 3T2–Adipocytes," *Cell*, 35:657–666 (1983).

Mendoza, et al., "Thermal Regulation of Membrane Fluidity in *Escherichia coli*," *J. Biol. Chem.*, 258:2098–2101 (1983).

Mahajan, et al., "Cerulenin Inhibition of Lipid Synthesis and Its Reversal by Exogenous Fatty Acids in *Myocobacterium smegmatis* ATTC 607," *Can. J. Biochem. Cell Biol.*, 63:85–90 (1985).

Mahajan, et al., "Cerulenin Effect on Phospholipid Metabolism in *Mycobacterium smegmatis* ATTC 607," *Biochim. Biophys. Acta*, 795:493–498 (1984).

Hait, et al., "Inhibition of Growth of Leukemic Cells by Inhibitors of Calmodulin: Phenothiazines and Melittin," *Cancer Chemother. Pharmacol.*, 14:202–205 (1985).

Rainwater, et al., "Fatty Acid Biosynthesis in *Mycobacterium tuberculosis* var. bovis *Bacillus Calmette–Guerin*," *J. Biol. Chem.*, 260:616–623 (1985).

Abraham, et al., "Lipid Metabolism and Enzyme Activities In Hormone–Dependent Hormone–Independent Mammary Adenocarcinoma in GR Mice," *JNCI*, 77:233–239 (1986).

Chalbos, et al., "Cloning of cDNA Sequences Of a Progestin–regulated mRNA from MCF7 Human Breast Cancer Cells," *Nucl. Acids Res.*, 14:965–981 (1986).

Weiss, et al., "Fatty–Acid Biosynthesis in Man, a Pathway of Minor Importance," *Biol. Chem. Hoppe–Seyler*, 367:905–912 (1986).

Fujii, et al., "Effect of Cerulenin, an Inhibitor of Fatty Acid Synthesis, on the Immune Cytolysis of Tumor Cells," *Jpn. J. Exp. Med.*, 56:99–106 (1986).

Pawlak, et al., "Evaluation of Thioesterase II as a Serum Marker for Rat Mammary Cancer," *Cancer Research*, 46:4712–4719 (1986).

Nishida, et al., "Effect of Thiolactomycin on the Individual Enzymes of the Fatty Acid Synthase System in *Escherichia coli*," *J. Biochem.*, 99:1447–1454 (1986).

Hoberg, et al., "Characterization of Cerulenin–Resistant Mutants of *Candida albicans*," *Infection and Immunity*, 51:102–109 (1986).

Tomada, et al., "Inhibition of acyl–CoA Synthetase by Triacsins," *Biochim. Biophys. Acta*, 921:595–598 (1987).

Chalbos, et al., "Fatty Acid Synthetase and Its mRNA Are Induced By Progestins in Breast Cancer Calls" *J. Biol. Chem.*, 262:9923–9926 (1987).

Debs, et al., "Selective Enhancement of Pentamidine Uptake in the Lung by Aerosolization and Delivery in Liposomes," *Amer. Rev. Repir. Dis.*, 135:731–737 (1987).

McAllister, et al., "The Effect of Tumour Growth on Liver Pantothenate, CoA, and Fatty Acid Synthetase Activity in the Mouse," *Br. J. Cancer*, 57:83–86 (1988).

Wilder, et al., "Altered Metabolic Rate and Fatty Acid Distribution in Adriamycin Resistant P388 Cells," *Proceedings of AACR*, 29:318, Abstr. 1265 (1988).

Tisdale, et al., "Changes in Host Liver Fatty Acid Synthase in Tumour–Bearing Mice," *Cancer Letters*, 42:231–235 (1988).

Bolla, et al., "The Assembly of the Major Outer Membrane Protein OmpF of *Escherichia coli* Depends on Lipid Synthesis," *The EMBO Journal*, 7:3595–3599 (1988).

Harris, et al., "Inhibition of Phenolic Glycolipid–1 Synthesis in Extracellular *Mycobacterium leprae* as an Indicator of Antimicrobial Activity," *International Journal of Leprosy*, 56:588–591 (1988).

Debs, et al., "Lung–Specific Delivery of Cytokines Induces Sustained Pulmonary and Systemic Immunomodulation in Rats," *J. Immunol.*, 140:3482–3488 (1988).

Spydevold et al., "Activities of Enzymes of Lipid Metabolism in Morris Hepatoma," *Biochim. Biophys. Acta*, 1003:80–83 (1989).

Chambon, et al., "Progestins and Androgens Stimulate Lipid Accumulation In T47D Breast Cancer Cells Via Their Own Receptors," *J. Steroid Biochem.*, 33:915–922 (1989).

Funabashi, et al., "Binding Site of Cerulenin in Fatty Acid Synthetase," *J. Biochem.*, 105:751–755 (1989).

Wall, et al., "Covalent Reaction of Cerulenin at the Active Site of acyl–CoA Reductase of *Photobacterium phosphoreum*," *Biochem. Cell Biol.*, 67:163–167 (1989).

Joyeux, et al., "Progestin Increases Gene Transcription and Messenger Ribonucleic Acid Stability of Fatty Acid Synthetase in Breast Cancer Cells," *Molecular Endocrinology*, 4:681–686 (1989).

Byers, et al., "Inhibition of *Vibrio harveyi* Bioluminescence by Cerulenin: In Vivo Evidence for Covalent Modification of the Reductase Enzyme Involved in Aldehyde Synthesis," *J. Bacteriol.*, 171:3866–3871 (1989).

Montgomery, et al., "Aerosolized Pentamidine as Second Line Therapy in Patients with AIDS and *Pneumocystis carinii* Pneumonia," *Chest*, 95:747–750 (1989).

Escot, et al., "Regulation of Fatty Acid Synthetase Ribonucleic Acid In The Human Endometrium During the Menstrual Cycle," *J. Clin Endocrinol. Metab.,* 70:1319–1324 (1990).

Joyeux, et al., "Effects of Progestins and Menstrual Cycle on Fatty Acid Synthetase and Progesterone Receptor in Human Mammary Glands," *J. Clin. Endocrinol. Metab.,* 70:1438–1444 (1990).

Chalbos, et al., "Expression of the Progestin–Induced Fatty Acid Sythetase in Benign Mastopathies and Breast Cancer as Measured by RNA In Situ Hybridization," *JNCI,* 82:602–606 (1990).

Chalbos, et al., "Progestin–Induced Fatty Acid Synthetase in Breast Cancer," *Ann. N. Y. Acad. Sci.,* 595:67–73 (1990).

Hourdou, et al., "Specific Inhibition of Iturin Biosynthesis by Cerulenin," *Can. J. Microbiol.,* 36:164–168 (1990).

Amy, et al., "Molecular Cloning of the Mammalian Fatty Acid Synthase Gene and Identification of the Promoter Region," *Biochem. J.,* 271:675–679 (1990).

Ried, et al., "Role of Lipopolysaccharide in Assembly of *Escherichia coli* Outer Membrane Proteins OmpA, OmpC, and OmpF," *J. Bacteriol.,* 172:6048–6053 (1990).

Debs, et al., "Regulation of Gene Expression in Vivo by Liposome–mediated Delivery of a Purified Transcription Factor," *J. Biol. Chem.,* 265:10189–10192 (1990).

Chalbos, et al., "The Anti–progestin RU486 Stabilizes the Progestin–induced Fatty Acid Synthetase mRNA but Does Not Stimulate Its Transcription," *J. Biol. Chem.,* 266:8220–8224 (1991).

Tomada, et al., "Evidence for an Essential Role of Long Chain Acyl–CoA Synthetase in Animal Cell Proliferation," *J. Biol. Chem.,* 266:4214–4219 (1991).

Ookhtens, et al., "Liver and Adipse Tissue Contributions to Newly Formed Fatty Acids in an Ascites Tumor", American Journal of Physiology (1984) Jul.;247(1 Pt 2):R146–53.

Mathur, et al., "Molecular Cloning and Sequencing of the Gene for Mycocerosic Acid Synthase, a Novel Fatty Acid Elongating Multifunctional Enzyme, from *Mycobacterium tuberculosis* var. bovis *Bacillus Calmette–Guerin,*" *J. Biol. Chem.,* 267:19388–19395 (1992).

Park et al., "Methylenolactocin, A Novel Antitumor Antibiotic from Penicillium SP.", The Journal of Antibiotics, vol. XLI, No. 6, pp. 751–758.

Murta, et al., "Synthesis and Asolute Stereochemistry of (–)–Protolichesterinic Acid, Antitumor Antibiotic Lactone from *Cetraria islandica*", J. Org. Chem. 1993, 58, pp. 7537–7541.

Shimada, et al., "Ring–Opening Aldol–Type Reaction of 2,2–Dialkoxycyclopropanecarboxylic Esters with Carbonyl Compounds. 3. The Diastereoselective Synthesis of 2,3, 4–Trisubstituted γ–Lactones[1]", J. Org. Chem. 1993, 58, pp. 5226–5234.

Cavallito, et al., "Lactone Aliphatic Acids as Antibacterial Agents", JACS, vol. 70, pp. 3724–3726.

de Azevedo, et al., "Novel, Enantiomerse Lactone Construction. First Synthesis of Methylenolactocin Antitumor Antibiotic from Penicillium sp.," *J. Org. Chem.* 57:4567–4569 (1992).

Pitot, et al., "Contribution of the Morris Hepatomas to the Biochemistry of Cancer—Establishment of the Phenotypic Heterogeneity of Neoplasms In Vivo", Progress in Cancer Research and Therapy, vol. 1, Raven Press (1976).

Schroering, et al., "Fatty Acid Synthetase in Chemically Induced Mammary Carcinomas," Research Communications in Chemical Pathology and Pharmacology, vol. 9, No. 4, Dec. 1974, pp. 775–778.

Ceriani, et al., "Immunohistochemical Studies in Breast Cancer Using Monoclonal Antibodies Against Breast Epithelial Cell Components and with Lectins," Dev. Oncol. 34:233–63 (1985).

Ziegler, et al., "Current Status of Adjuvant Therapy of Early Breast Cancer", Americal Journal of Clinical Oncology, Apr. 1991, vol. 14, No. 2, pp. 101–110 (Abstract).

Redston, et al., "Expression of OA519 (Haptoglobin–Related Protein Epitopes) in Colorectal Carcinomas: Comparison with Molecular Genetic Alterations and Metastasis," The Johns Hopkins University School of Medicine and Hospital, Baltimore, MD Abstracts 272, p. 47A.

Lin, et al., "Fatty Acid Synthetase from a Mouse Mammary Adenocarcinoma[1]," Cancer Research 35, Nov. 1975. pp. 3094–3099.

Abraham, et al., "Lipids and Lipogenesis in a Murine Mammary Neoplastic System," Control Mechanisms in Cancer, Raven Press (1976) pp. 363–378.

Ahmad, et al., "Increase in Fatty Acid Synthetase Content of 3T3–L Cells Undergoing Spontaneous and Chemically Induced Differentiation to Adipocytes," Biochem. J. (1979) 182:509–514.

Pawlak, et al., "Evaluation of Thioesterase II as a Serum Marker for Rat Mammary Cancer[1]", Cancer Research 46, Sep. 1986, pp. 4712–4719.

Ahmad, et al., "Inactivation of Rat Mammary Gland Fatty Acid Synthetase By S–(4–bromo–2,3–dioxobutyl)–Coenzyme," Fed. Proc. (1981) 40:1794, Abstract 1463.

Kuhajda, et al., "The Distribution of Carcinoembryonic Antigen in Breast Carcinoma," Cancer (1983), 52:1257–1264.

Kuhajda, et al., "Pregnancy–Specific Beta–1 Glycoprotein (SP–1) in Breast Carcinoma," Cancer (1984), 54:1392–1396.

Kuhajda, et al., "Pregnancy–Associated Plasma Protein A:A Clinically Significant Predictor of Early Recurrence in State II Breast Carcinoma," Hum. Pathol. (1985), 16:228–235.

Kuhajda, et al., "Pregnancy–Associated Plasma Protein A:A Clinically Significant Predictor of Early Recurrence in Stage I Breast Carcinoma is Independent of Estrogen Receptor Status," Am. J. Pathol. (1985), 121:342–348.

Kuhajda, et al., "Molecular Characterization of a Human Breast Cancer Antigen Predicting Early Relapse," Lab. Invest. (1987) vol. 56, Abstract 236.

Kuhajda, et al., "Expression of Haptoglobin–Related Protein and its Potential Role as a Tumor Antigen," Proc Natl. Acad. Sci. USA (1989), 86:1188–1192.

Kuhajda, et al., "Haptoglobin–Related Protein (Hpr) Epitopes in Breast Cancer as a Predictor of Recurrence of the Disease," N. Eng. J. Med. (1989) 321:636–641.

Shurbaji, et al., "Immunohistochemical Expression of Hpr In Primary and Metastatic Breast Carcinoma," Lab. Invest., 60:1, Abstract 525 (1989).

Pasternack, et al., "Expression of Haptoglobin–related Protein (Hpr) Epitopes in Human Breast Carcinoma Correlates with Increased Phenotypic Malignancy," J. Cell. Biochem. 13B:137, Abstract E410 (1989).

Shurbaji, et al., "Expression of Haptoglobin Related Protein (Hpr) Epitopes by Prostate Carcinoma: A Potential Prognostic Indicator," Intl. Acad. Pathol. Mtg., Mar. 1991, Abstract 300.

Corrigan, et al., "Prognostic Value of the Immunohistochemical Demonstration of Haptoglobin–Related Protein in Breast Cancer," A.J.C.P., Sep. 1991, p. 406, Abstract 19.

Cote, et al., "Prognostic Features in Breast Carcinoma: Detection of Occult Axillary Lymph Node Micrometastases (LNM), Expression of Haptoglobin Related Binding Protein (OA519) and Progesterone Receptor (PR) in Primary Tumors," Lab. Invest., 66:13A (1992), Abstract 66.

Martin, et al., "Immunohistochemical Expression of OA–519 in Pre–Neoplastic and Neoplastic Lesion Polyps of the Colon," American Society for Clinical Oncology (Abstract submitted for San Diego Meeting).

Shurbaji, et al., "Expression of Oncogenic Antigen 519 (OA–519) in Prostate Cancer is a Potential Prognostic Indicator," Am. J. Clin. Pathol., 97:686–691 (1992).

INHIBITION OF FATTY ACID SYNTHASE AS A MEANS TO REDUCE ADIPOCYTE MASS

This application is a Continuation of Provisional application 60/006,940 filed Nov. 17, 1995.

BACKGROUND OF THE INVENTION

1. Field of the Invention

This invention concerns the systemic administration of an inhibitor of fatty acid synthase (E.C. 2.3.1.85, FAS) by any suitable route to achieve weight loss and/or reduction of adipocyte mass without significant toxicity. Use of FAS inhibitors for this purpose is not restricted to humans or any species, but includes reduction of adipocyte mass in livestock and poultry. This invention also concerns the synthesis of a family of compounds (α-methylene-β-carboxy-γ-butyrolactones) which are fatty acid synthesis inhibitors, and the use of these compounds to achieve weight loss, to treat susceptible cancer cells, or in other applications characteristic of FAS inhibitors.

2. Review of Related Art

Compounds and proteins which induce reduction of weight or adipocyte mass in mammals may act through the following mechanisms: [1] increased fat mobilization, such as human chorionic gonadotrophin (HCG) induced metabolism of fat stores (Bray, et al., "Nutritional Support of Medical Practice," Harper and Row, Philadelphia, 1983); [2] increased calorigenesis, such as that induced by thyroid hormone (Abraham et al., 1985, *Int. J. Obes.*, 9:433–42); [3] decreased appetite, induced by anorexic agents such as felbamate and dexfenfluramine (McTavish et al., 1992, *Drugs*, 43:713–33); [4] decreased lipogenesis (see Table 1 below); and [5] mutated or decreased blood levels of the ob gene product (Halaas et al., 1995, *Science*, 269:543–546). In mice (Kannan et al., 1980, *Lipids*, 15:993–8) and man, significant fatty acid synthesis occurs in liver (Triscari et al., 1985, *Metabolism*, 34:580–7; Barakat et al., 1991, *Metabolism*, 40:280–5) and adipose tissue (Goldrick et al., 1974, *Clin. Sci. Mol. Med.*, 46:469–79), and rates of fatty acid synthesis are higher in obese mice or humans (Angel et al., 1979, *Eur. J. Clin. Invest.*, 9:355–62; Belfiore et al., 1976, *Metabolism*, 25:483–93). Hence, it is not surprising that a number of weight reducing agents reduce de novo fatty acid synthesis. Table 1 provides a list of agents known to both inhibit lipogenesis and induce weight loss.

TABLE 1

Compounds Which Induce Weight Loss

| COMPOUND | ENZYME TARGET and TYPE OF INHIBITION | REFERENCES and SPECIES STUDIED |
| --- | --- | --- |
| TPIA & CPIB | acetyl-CoA carboxylase, mixed competitive and (non-competitive) | Maragoudakis, 1969, J. Biol. Chem, 244: 5005–13 (rodent study) |
| Sodium 2-n-pentadecylbenzimidazole-5-carboxylate | acetyl-CoA carboxylase, (competitive (?)) | Whittington et al., 1987, Int. J. Obes., 11: 619–29 (rodent study) |
| Dehydroepiandosterone | glucose-6-phosphate dehydrogenase, (competitive) | Yen et al., 1981, Lipids, 12: 409–13 (rodent study) |
| (−) hydroxycitrate | ATP citrate lyase, (competitive) | Greenwood et al., 1981, Am. J. Physiol., 240: E72–8. (rodent study) |

TABLE 1-continued

Compounds Which Induce Weight Loss

| COMPOUND | ENZYME TARGET and TYPE OF INHIBITION | REFERENCES and SPECIES STUDIED |
| --- | --- | --- |
| 30 kD protein | enzyme target unknown, inhibits FA synthesis | Harris, et al., 1989, Am. J. Physiol., 257: R326–36 (rodent study) |
| ob gene product | protein produced by adipocytes which inhibits appetite | Halaas et al., 1995, Sciences, 269: 543–6 (rodent study) |

Interestingly, no inhibitors of fatty acid synthase (FAS) (E.C. 2.3.1.85) are mentioned in prior art as agents which produce weight loss.

SUMMARY OF THE INVENTION

It is an object of this invention to provide a method for inducing weight reduction focused on a new therapeutic target.

It is a further object of this invention to provide novel compounds that inhibit the activity of FAS; in particular, compounds with increased bioavailability and very low toxicity, compared to previously available FAS inhibitory compounds.

This invention provides a method for inducing weight loss in an animal comprising administering to the animal a compound which reduces fatty acid synthase (FAS) activity in adipocytes or liver cells, the compound being other than a fat or a metabolizable product of a fat (i.e., the compound does not inhibit FAS through product inhibition). In an alternative embodiment, this invention provides a method for treating a condition responsive to reduction in adipose tissue mass in an animal comprising administering to the animal a composition which reduces fatty acid synthase (FAS) activity in adipocytes or liver cells, wherein the composition does not contain a fatty acid or fatty acid residue. The condition treated by this method may be obesity or non-insulin dependent diabetes mellitus. Preferably, the composition contains a specific inhibitor of FAS, or the composition inhibits biosynthesis of FAS. The composition may be administered in an amount sufficient to reduce adipocyte mass in the animal, or in an amount sufficient to reduce FAS activity in liver cells of the animal.

In another embodiment, this invention provides a method for inducing weight loss in an animal comprising administering to the animal an inhibitor of fatty acid synthase (FAS), the FAS inhibitor preferably being administered in an amount sufficient to reduce fatty acid synthesis in adipose tissue or liver.

In another embodiment, this invention provides a pharmaceutical composition comprising a 5-substituted 2-oxo-3-methylene-4-furancarboxylic acid, wherein the substituent is selected from:

(a) a saturated linear alkyl group of 3–18 carbons;

(b) a saturated branched alkyl group of 3–18 carbons;

(c) an unsaturated linear or branched alkyl group of 3–18 carbons;

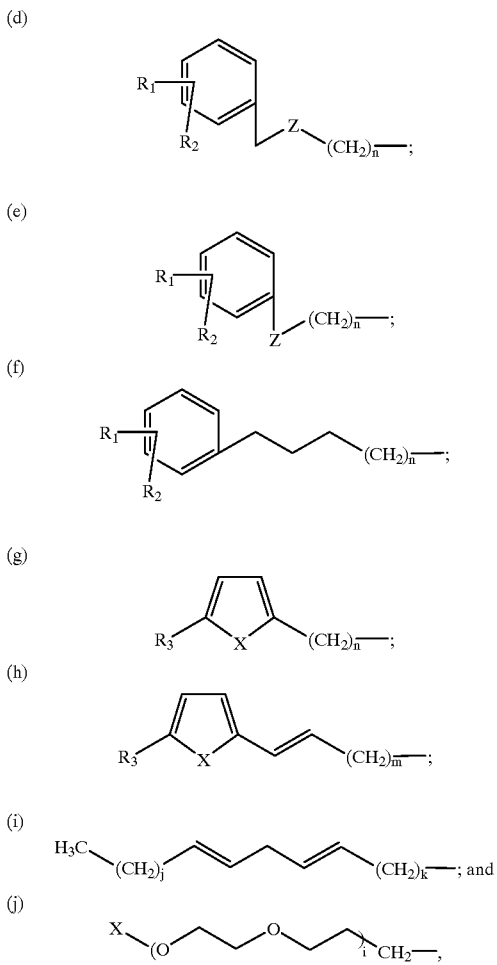

wherein R1 and R2 each are H, $CH_3$, $C_2H_5$, $C_3H_7$, $C_4H_9$, $CF_3$, $OCH_3$, F, Cl, or Br; R3 is H, $CH_3$, $C_2H_5$, $C_3H_7$, $C_4H_9$, COOH, $COOCH_3$, $COOC_2H_5$, $COOC_3H_7$, or $COOC_4H_9$; R4 is H, $CH_3$, $C_2H_5$, $C_3H_7$, $C_4H_9$; X is N, S or O; Z is $CH_2$, O, NH or S; i is 1 to 5; j is 0 to 10; k is 1 to 10;m is 1–13; and n is 1 to 15, and R1 and R2 may be the same or different. In a preferred embodiment, the substituent is $C_4H_9$, $C_5H_{11}$, $C_6H_{13}$, $C_7H_{15}$, $C_8H_{17}$, $C_9H_{19}$, $C_{10}H_{21}$, $C_{12}H_{25}$, $C_{14}H_{29}$, $C_{15}H_{31}$, $C_{16}H_{33}$, $C_{17}H_{35}$, $C_{18}H_{37}$, 3E-4-(3-fluorophenyl) or 3E,6E-octadienyl. In a particularly preferred embodiment, the substituent is n-octyl.

In another embodiment, this invention provides a method for inducing weight loss in an animal comprising administering to the animal the pharmaceutical composition containing the 5-substituted 2-oxo-3-methylene-4-furancarboxylic acid.

In yet another embodiment, this invention provides a method of inhibiting growth of tumor cells in an animal, said cells expressing at least one enzyme of the fatty acid biosynthetic pathway, comprising administering the pharmaceutical composition containing the 5-substituted 2-oxo-3 -methylene-4-furancarboxylic acid to the tumor cells. Typically the tumor cells are cells which express fatty acid synthase (FAS), and preferably, the composition is administered in an amount specifically cytotoxic to said tumor cells.

No literature prior to the present studies has identified FAS as a target enzyme for weight reduction. However, we have noted weight loss in nude mice treated with cerulenin, a non-competitive inhibitor of FAS. Sustained reduction of adipocyte mass in humans without toxicity would significantly impact disease prevention world-wide. Aside from psychological and self-esteem improvement, weight loss via reduction of adipocyte mass may [1] ameliorate hyperglycemia associated with non-insulin-dependent diabetes mellitus thereby reducing diabetic complications such as arterial disease, blindness, cataracts, etc., [2] reduce hypertension, [3] reduce risk of coronary artery vascular disease and stroke, and [4] reduce the risk of other complications of massive obesity such as osteoarthritis, surgical complications, etc. There is also potential use in livestock and poultry to reduce the saturated fat content of meat products. Therefore FAS inhibitors are disclosed herein as novel agents for weight reduction.

A family of compounds (γ-substituted-α-methylene-β-carboxy-γ-butyrolactones) whose synthesis was based on the cerulenin motif is shown herein to inhibit fatty acid synthesis, inhibit growth in certain susceptible tumor cells, and induce weight loss. The α-methylene-β-carboxy-γ-butyrolactones have several advantages over the natural product cerulenin for therapeutic applications: [1] they do not contain the highly reactive epoxide group of cerulenin, [2] they are stable and soluble in aqueous solution, [3] they can be produced by a two step synthetic reaction and thus easily produced in gram quantities, and [4] they are easily tritiated to high specific activity for biochemical and pharmacologic analyses. Thus, this family of compounds is disclosed herein for these therapeutic applications.

DETAILED DISCLOSURE OF THE INVENTION

Figure 1:
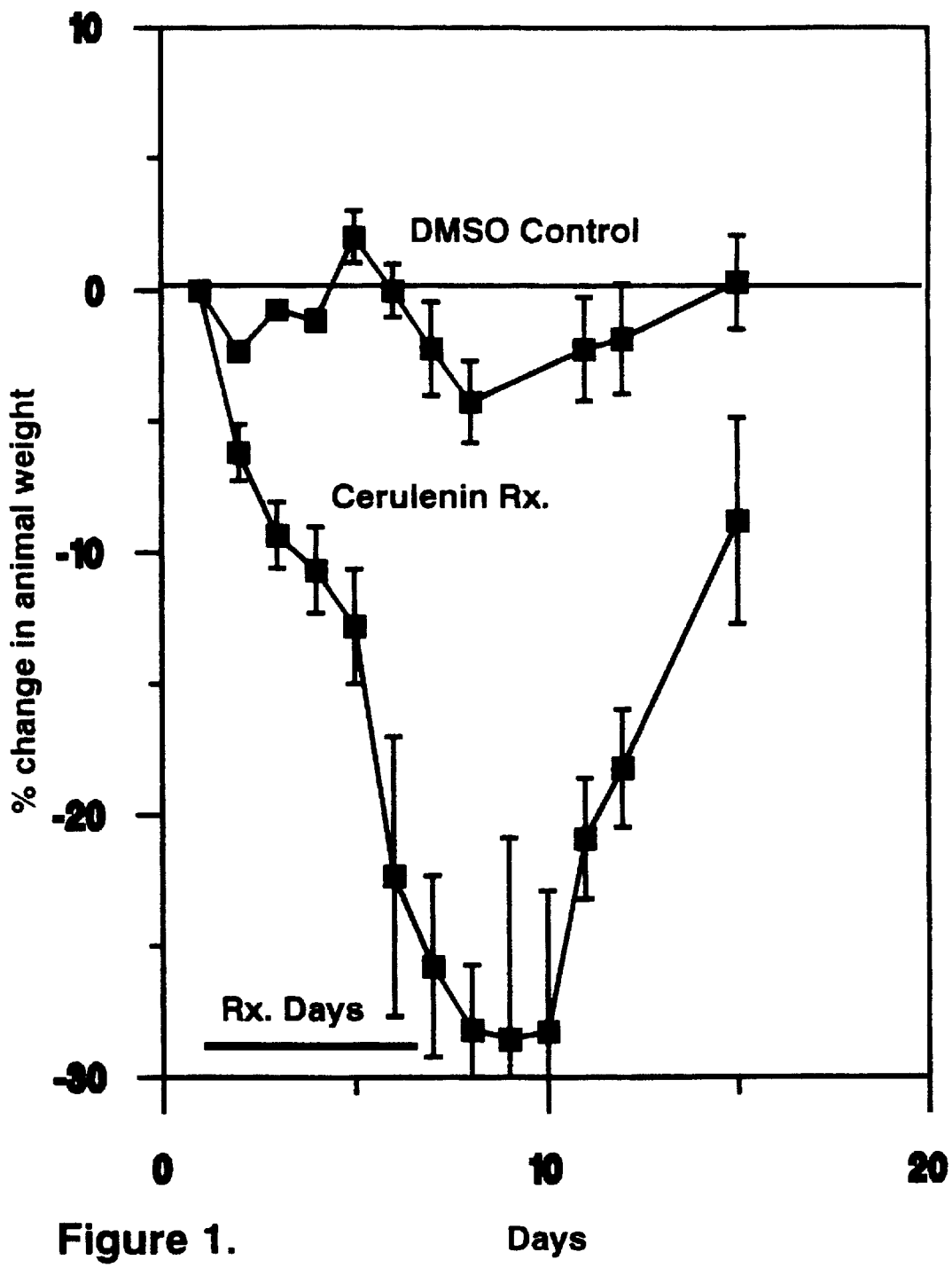
FIG. 1 shows induction of weight loss in nude mice by cerulenin.

This invention describes: [1] the use of inhibitors of fatty acid synthase (E.C. 2.3.1.85, FAS), such as the inhibitor cerlenin, as a means to reduce body weight; [2] the synthesis of a family of compounds (α-methylene-β-carboxy-γ-butyrolactones) which are fatty acid synthesis inhibitors; [3] the use of α-methylene-β-carboxy-γ-butyrolactone fatty acid synthesis inhibitors as a means to treat tumor cells expressing FAS; [4] the use of α-methylene-β-carboxy-γ-butyrolactone fatty acid synthesis inhibitors as a means to reduce body weight; and [5] the use of any fatty acid synthase inhibitors to systematically reduce adipocyte mass (adipocyte cell number or size) as a means to reduce body weight.

FAS Inhibitors

FAS inhibitors contemplated by this invention are compounds that directly reduce the activity of FAS in animal cells without any significant (direct) effect on other cellular activities, at least at comparable concentrations. A wide variety of compounds have been shown to inhibit fatty acid synthase (FAS), and selection of a suitable FAS inhibitor for use in this invention is within the skill of the ordinary worker in this art. Compounds which inhibit FAS can be identified by testing the ability of a compound to inhibit fatty acid synthase activity using purified enzyme. Fatty acid synthase activity can be measured spectrophotometrically based on the oxidation of NADPH, or radioactively by measuring the incorporation of radiolabeled acetyl- or malonyl-CoA. (Dils, et al, *Methods Enzymol,* 35:74–83). FAS inhibitors are exemplified in U.S. patent application Ser. No. 08/188,425 and International patent publication WO 94/02108, both of which are incorporated herein by reference.

Suitable FAS inhibitors may be identified by a simple test exemplified in Example 7, and in U.S. patent application Ser. No. 08/188,425. Generally, this test uses a tumor cell line in which an FAS inhibitor, typically cerulenin, is cytotoxic. Such cell lines include SKBR-3, ZR-75-1, and preferably HL60. Suitable FAS inhibitors will inhibit growth of such cell lines, but the cells are rescued by exogenous supply of the product of the FAS enzyme (fatty acid). When cell growth is measured in the presence and absence of exogenous fatty acid (e.g., palmitate or oleate), inhibition by specific FAS inhibitors is relieved by the fatty acid.

Alternatively, suitable FAS inhibitors can be characterized by a high therapeutic index. Inhibitors can be characterized by the concentration required to inhibit fatty acid synthesis in cell culture by 50% ($IC_{50}$ or $ID_{50}$). FAS inhibitors with high therapeutic index will inhibit fatty acid synthesis at a lower concentration (as measured by $IC_{50}$) than the $IC_{50}$ for inhibition of cell growth in the presence of exogenous fatty acid. Inhibitors whose effects on these two cellular activities show greater differences are more preferred. Preferred inhibitors of fatty acid synthesis will have $IC_{50}$ for fatty acid synthetic activity that is at least 1 log lower, more preferably at least 2 logs lower, and even more preferably at least 3 logs lower than the inhibitor's $IC_{50}$ determined for cell growth.

Therapy with FAS Inhibitors

Fatty acid synthesis inhibitors, especially FAS inhibitors, will block the body's ability to convert carbohydrates to fat. On a fat restricted diet, this will lead to a reduction of storage fat. In addition, it will lead to decreased intracellular fat storage and a reduction in adipocyte mass. This may be expected to have the primary and/or secondary effects listed in Table 2. Fatty acid synthesis inhibition will lead to reduction in hepatic fat, and this in turn can lead to reduction in the rate or incidence of cirrhosis in alcoholics (see, e.g., French, 1989, *Clinical Biochemistry,* 22:41–9; Clements, et al., 1995, *Am. J. Respir. Crit. Care Med.,* 151:780–784, incorporated herein by reference). Increased insulin responsiveness is a direct consequence of decreased adipocyte mass. Reduced adipocyte mass will reduce the risk of arterial vascular disease, stroke, etc. Thus, the method of this invention is particularly applicable to overweight individuals, diabetics, and alcoholics. The method is generally useful as part of a program to treat obesity and complications thereof.

Table 2. Effects of Decreased Intracellular Fat Storage and Reduction in Adipocyte Mass Weight loss without muscle loss
Reduction in hepatic fat
Increased insulin responsiveness (especially in Type II diabetes mellitus)
Decreased blood pressure
Decreased arterial vascular disease
Decreased susceptibility to liver injury associated with fatty change, including endotoxin mediated liver injury The method of the present invention for inducing weight loss is applicable to animals, including vertebrates, especially mammals. Animals particularly contemplated include food animals such as poultry, swine, cattle, sheep, and other animals where reduction in fat accumulation without reduction in muscle mass may be desirable for veterinary health or economic reasons. Similarly, FAS inhibitors may be administered according to the method of this invention to dogs, cats, horses and other animals for veterinary health reasons, particularly reasons analogous to the reasons given herein for medical therapeutic use of this invention. Dosing protocols for the FAS inhibitors according to this method may be adapted to various animals from the medical procedures and the in vitro and in vivo data provided herein, in view of standard veterinary pharmacological principles. Generally, this method will not be applied to lactating animals.

Treatment according to this invention involves administering a compound according to this invention (an FAS inhibitor and/or an α-methylene-β-carboxy-γ-butyrolactone) to the subject of treatment. The pharmaceutical compositions containing any of the compounds of this invention may be administered by parenteral (subcutaneously, intramuscularly, intravenously, intraperitoneally, intrapleurally, intravesicularly or intrathecally), topical, oral, rectal, or nasal route, as necessitated by choice of drug and disease.

Therapeutic compounds according to this invention are preferably formulated in pharmaceutical compositions containing the compound and a pharmaceutically acceptable carrier. The concentrations of the active agent in pharmaceutically acceptable carriers will depend on solubilities. The dose used in a particular formulation or application will be determined by the requirements of the particular type of disease and the constraints imposed by the characteristics and capacities of the carrier materials. The pharmaceutical composition may contain other components so long as the other components do not reduce the effectiveness of the compound according to this invention so much that the therapy is negated. Pharmaceutically acceptable carriers are well known, and one skilled in the pharmaceutical art can easily select carriers suitable for particular routes of administration (see, e.g., *Remington's Pharmaceutical Sciences,* Mack Publishing Co., Easton, Pa., 1985). Dose and duration of therapy will depend on a variety of factors, including the therapeutic index of the drugs, disease type, patient age, patient weight, and tolerance of toxicity. Dose will generally be chosen to achieve serum concentrations from about 1 ng to about 100 μg/ml, typically 0.1 μg/ml to 10 μg/ml. Preferably, initial dose levels will be selected based on their ability to achieve ambient concentrations shown to be effective in in-vitro models, such as that used to determine therapeutic index, and in-vivo models and in clinical trials, up to maximum tolerated levels. Standard clinical procedure prefers that chemotherapy be tailored to the individual patient and the systemic concentration of the chemotherapeutic agent be monitored regularly. The dose of a particular drug and duration of therapy for a particular patient can be determined by the skilled clinician using standard pharmacological approaches in view of the above factors. The response to treatment may be monitored by analysis of blood or body fluid levels of the compound according to this invention, measurement of activity if the compound or its levels in relevant tissues or monitoring disease state in the patient. The skilled clinician will adjust the dose and duration of therapy based on the response to treatment revealed by these measurements.

The compositions described above may be combined or used together or in coordination with another therapeutic substance. The inhibitor of fatty acid synthesis, or the synergistic combination of inhibitors, will of course be administered at a level (based on dose and duration of therapy) below the level that would kill the animal being treated. Preferably, administration will be at a level that will not irreversibly injure vital organs, or will not lead to a permanent reduction in liver function, kidney function, cardiopulmonary function, gastrointestinal function, genitourinary function, integumentary function, musculoskeletal function, or neurologic function. On the other hand, administration of inhibitors at a level that kills some cells which will subsequently be regenerated (e.g., endometrial cells) is not necessarily excluded.

Suppression of FAS Biosynthesis

While the FAS inhibitors discussed herein are typically small molecule compounds that directly inhibit the enzyme, it will be readily apparent to the skilled clinician that specific prevention of FAS biosynthesis is an equivalent procedure which will accomplish the same desired result. Therefore, this invention also contemplates inhibition of FAS biosynthesis as a method for treating obesity, etc. This may be accomplished by selectively degrading mRNA encoding FAS or otherwise interfering with its transcription and/or translation. This may be accomplished, for instance, by introduction of a ribozyme specific for FAS mRNA (see, e.g., Czubayko, et al., 1994, *J. Biol. Chem.*, 269:21358–21363, incorporated herein by reference, for ribozyme methodology). This may alternatively be accomplished by antisense RNA complementary to the nucleic acid sequence of FAS. The sequence of human FAS is disclosed in U.S. patent application Ser. No. 08/188,426, incorporated herein by reference. Typically, antisense therapy involves an expression vector containing at least a portion of the sequence encoding human FAS operably linked to a promoter such that it will be expressed in antisense orientation. As a result, RNA which is complementary to and capable of binding or hybridizing to FAS mRNA will be produced. Upon binding to mRNA for FAS, translation of that mRNA is prevented, and consequently FAS is not produced. Production and use of antisense expression vectors is described in more detail in U.S. Pat. No. 5,107,065 and U.S. Pat. No. 5,190,931, both of which are incorporated herein by reference.

The expression vector material is generally produced by culture of recombinant or transfected cells and formulated in a pharmacologically acceptable solution or suspension, which is usually a physiologically-compatible aqueous solution, or in coated tablets, tablets, capsules, suppositories, inhalation aerosols, or ampules, as described in the art, for example in U.S. Pat. No. 4,446,128, incorporated herein by reference. The vector-containing composition is administered to a mammal in an amount sufficient to transfect a substantial portion of the target cells of the mammal. Administration may be any suitable route, including oral, rectal, intranasal or by intravesicular (e.g. bladder) instillation or injection where injection may be, for example, transdermal, subcutaneous, intramuscular or intravenous. Preferably, the expression vector is administered to the mammal so that the tumor cells of the mammal are preferentially transfected. Determination of the amount to be administered will involve consideration of infectivity of the vector, transfection efficiency in vitro, immune response of the patient, etc. A typical initial dose for administration would be 10–1000 micrograms when administered intravenously, intramuscularly, subcutaneously, intravesicularly, or in inhalation aerosol, 100 to 1000 micrograms by mouth, or $10^5$ to $10^{10}$ plaque forming units of a recombinant vector, although this amount may be adjusted by a clinician doing the administration as commonly occurs in the administration of other pharmacological agents. A single administration may usually be sufficient to produce a therapeutic effect, but multiple administrations may be necessary to assure continued response over a substantial period of time.

Further description of suitable methods of formulation and administration according to this invention may be found in U.S. Pat. Nos. 4,592,002 and 4,920,209, incorporated herein by reference.

Synthesis of $\alpha$-methylene-$\beta$-carboxy-$\gamma$-butyrolactones

While experiments with cerulenin demonstrate that a fatty acid synthesis inhibitor induces both weight and adipocyte mass reduction in vivo, the bioavailability of cerulenin is limited, and this in turn may limit its use as a drug in humans. Rational design and synthesis of novel compositions of matter has lead to fatty acid synthesis inhibitors which have increased potency and stability in vivo. The design of inhibitors/inactivators of FAS is predicated upon: [1] an understanding of the mechanism of fatty acid biosynethesis, in particular that of the critical ketosynthase or "condensing enzyme" domain of this polyfunctional enzyme (Wakil, S. J., 1989, *Biochemistry*, 28:4523–4530; Funabashi et al., 1983, *Tetrahedron*, 24:2673–2676) and, [2] the well-studied inactivation of FAS by the natural product cerulenin (Funabashi et al., 1989, *J. Biochem.*, 105:751–755).

In fatty acid biosynthesis the characteristic two-carbon chain extension is carried out by FAS. Malonate, bound as its thioester to the pantetheine arm of acyl carrier protein (ACP), enters the active site where the elongating fatty acid chain is bound to a highly reactive cysteine residue of the enzyme. The malonyl ACP is decarboxylated to give a reactive enolate anion, which attacks the cysteine-bound acyl group. The transiently generated tetrahedral oxyanion rapidly decomposes to regenerate the free enzyme cysteine thiolate and the homologated $\beta$-ketoacyl intermediate bound to ACP. The chemical complexity of these steps, that is (a) the role and mechanism of decarboxylation, (b) the generation of an oxyanion intermediate and (c) the presence of a highly reactive cysteine thiol(ate) in the catalytic cycle, make these steps in the biosynthesis especially attractive for drug design.

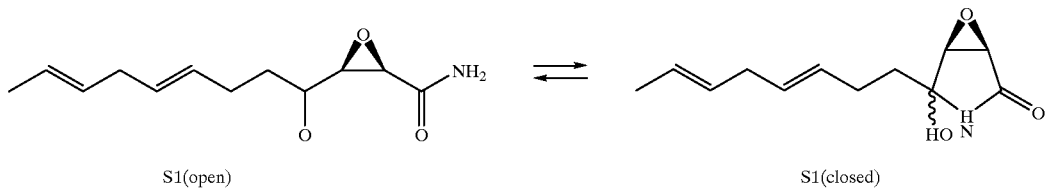

S1(open) ⇌ S1(closed)

Nature chose to target the ketosynthase step of FAS in the natural antibiotic cerulenin (S1). Cerulenin exists in solution as a equilibrium between an open (S1-open) and closed form (S1-closed). Cerulenin is a potent inactivator of FAS and is known to covalently bind to the reactive cysteine residue of the ketosynthase domain. (Funabashi et al., 1989; D'Angnolo et al., 1973, *Biochim. Biophys. Acta*, 326:155–166; Siggaard-Andersen et al., 1991, *Proc. Natl. Acad. Sci. USA*, 88:4114–4118).

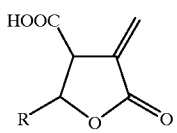

S2

Simple molecular modeling exercises and structure-based searches based on the mechanism outlined above and in the key chemical elements noted above have yielded a small number of lead compounds, some known to possess FAS inhibitory properties specifically or antimicrobial/antitumor activities more generally. Among these was a group of α-methylene lactones of the general structure S2: protolichesteric acid (S2, R=$C_{13}H_{27}$) (Berdy, J., 1982, "Anonymous Handbook of Antibiotic Compounds", *CRC Press*,pp. 39–53), allo-perusaric acid (S2, R=$C_{13}H_{26}$ $COCH_3$) (Huneck et al., 1986, *Phytochem.*, 25:543–549), nephromopsinic acid (S2, R=$C_{11}H_{23}$) (Berdy, 1982) and methylenolactocin (S2, R=$C_3H_7$) (Park et al., 1988, *Antibiotics*, 41:751–758). The last of these compounds, for example, has been isolated from a Penicillium species and found to possess antibacterial and antitumor activity ((Park et al., 1988), but the mechanism(s) of action is/are not understood. A series of derivatives of S2 containing side chains (R) of various lengths has been synthesized by the present inventors in recognition of the carboxylic acid and the suitably-placed electrophilic α-methylene lactone as potential inactivators of the ketosynthase of FAS.

A considerable body of synthetic information exists to prepare compounds of this structural type (Murta et al., 1993, *J. Org. Chem.*, 58:7537–7541; Azevedo et al., 1992, *J. Org. Chem.*, 57:4567–4569). Prominent among these was an impressively efficient route to the specific class represented by S2 reported by Carlson and Oyler (Carlson et al., 1976, *J. Org. Chem.*, 41:4065–4069). In this synthesis the dianion of 4-methoxybenzyl itaconate (S3) can be condensed with aldehydes (S4) of various chain description (R) to give in one step, after rapid exposure to strong acid, the desired α-methylene lactone carboxylic acid S2. Both the trans- and cis-isomers are generated slightly favoring the former. These diastereomers may be separated by flash silica gel chromatography using ethyl acetate:hexanes:acetic acid (30:70:1) as eluent and individually crystallized from boiling hexanes.

A series of derivatives of S2 has been prepared containing saturated alkyl, unsaturated alkyl and aryl-containing side chains (R)(e.g., —$C_6H_{23}$—$C_7H_{15}$—$C_8H_{17}$, —$C_9H_{19}$, —$C_{11}H_{23}$ and —$C_{13}H_{27}$). Based on their in vitro biological activity against HL60 cells, human breast cancer cell lines, and normal fibroblasts, the S2 compound with R=—$C_8H_{17}$ was chosen as a representative compound for further study. This compound, designated C-75 herein, coincidentally has an alkyl side chain approximately the length of cerulenin. C-75 has been prepared in crystalline form. For biochemical studies, radiolabeled S2 is readily accessible from the tritiated aldehyde S4 (H*=$^3$H), which is in turn easily available by reduction with sodium borohydride($^3$H) and reoxidation to the aldehyde. A substantial kinetic isotope effect in the latter reaction is well known and leads to high retention of the heavy isotope as demonstrated in earlier work from this laboratory (Townsend et al., 1986, *J. Chem. Soc. Chem. Commun.*, 638–639). If higher specific radioactivity is required, more elaborate catalytic tritiation of a carbon-carbon double bond could be carried out to give the aldehyde at very high specific activity.

The preparation of these compounds and survey of various structural types may be amenable to combinatorial methods by use of the resin supports S5 and S6.

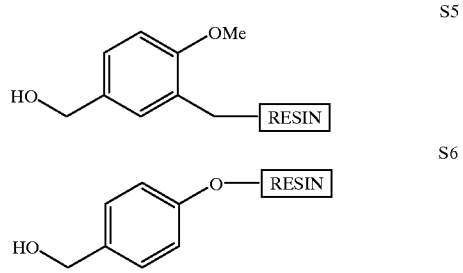

Esterification with itaconic anhydride would yield the ester corresponding to S3 ready for dianion formation and reaction with aldehydes S4. Unreacted aldehyde can be washed from the resin and the product obtained by acidification to cause cyclization to the lactone S2 and regeneration of the resins S5 and S6. Structural types of aldehydes represented above and by others should be assayed as described below to exclude inactive forms.

Alpha-methylene-β-carboxy-γ-butyrolactones, including tetrahydro-3-methylene-2-oxo-5-n-octyl-4-furancarboxylic acid (C-75), are easily and inexpensively synthesized and can be radiolabeled to high specific activity for in vivo pharmaokinetic analysis. Like cerulenin, C-75, and similar α-methylene-β-carboxy-γ-butyrolactones, will effectively inhibit the growth of tumor cells in vivo, particularly those such as OVCAR-3 cells which express high levels of FAS, and these compounds can be used in treating cancers containing such cells (see U.S. patent application Ser. No. 08/188,425, incorporated herein by reference).

EXAMPLES

In order to facilitate a more complete understanding of the invention, a number of Examples are provided below.

However, the scope of the invention is not limited to specific embodiments disclosed in these Examples, which are for purposes of illustration only.

Example 1

Synthesis of α-methylene-β-carboxy-γ-butyrolactones

This example illustrates the use of the 4-methoxybenzyl itaconate dianion S3 for preparation of several derivatives of type S2 and S2[1].

Example 1A

Preparation of p-methoxybenzyl itaconate

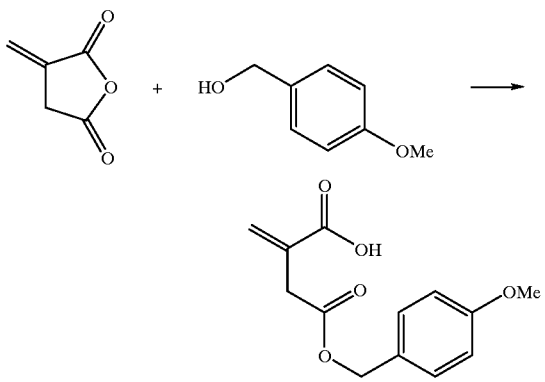

A mixture of itaconic anhydride (19 g, 0.169 mole) and p-methoxybenzyl alcohol (50 mL) was stirred in a 250 mL round-bottomed flask at 55–60° C. for 40 h. After cooling to room temperature, the reaction mixture was diluted with 150 mL of diethyl ether and the solution was poured into saturated aqueous sodium bicarbonate (200 mL). The layers were separated and the aqueous layer was acidified to pH 3 with conc. HCl. The precipitate formed was collected by filtration and dried in vacuuo. Recrystallization from ethyl acetate-hexane furnished 38 g of the desired ester as a white crystalline solid (90%); Mp 87.5° C. (lit 86.8–87.2° C., Carson, et al., 1976); IR (film) 3000–3400, 2935, 1720, 1681, 1634, 1612, 1515 cm$^{-1}$; $^1$H NMR δ(CDCl$_3$) 3.3 (s, 2H), 3.7 (s, 3H), 5.0 (s, 2H), 5.7 (d, 1H, J=0.8 Hzz), 6.43 (s, 1H), 6.80 (d, 2H, J=8.8 Hz), 7.24 (d, 2H, J=8.4 Hz).

Example 1B

Preparation of α-methylene lactone derivatives—typical procedure

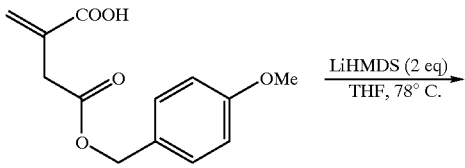

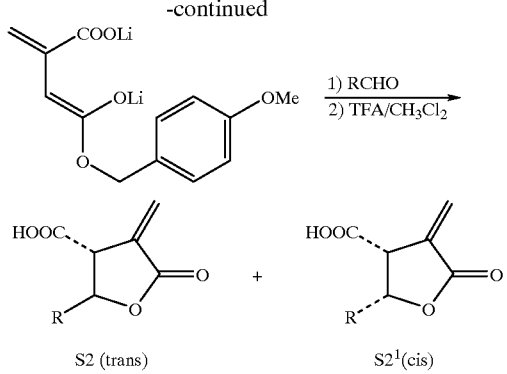

Lithiumhexamethyldisilyl amide (40 ML, 1M, 40 mmol) was added to a solution of 20 mmol of the itaconate half ester in 200 ML of anydrous THF cooled at −78° C. After stirring for 1 h, 20 mmol of the aldehyde (RCHO dissolved in 10 mL of anhydrous THF) was introduced to the reaction mixture through a cooled (−78° C.) cannula. After the addition, the solution was stirred at −78° C. for 3–4 h, and then the reaction was quenched with 20 mL of 6N H$_2$SO$_4$ and immediately extracted into either (250 mL). The ethereal solution was dried over anhydrous MgSO$_4$. The solution was filtered and evaporated under reduced pressure yielding a gummy solid. This crude product was taken up in CH$_2$Cl$_2$ (100–125 mL) and treated with 1.5 mL of trifluoroacetic acid. The mixture was stirred at room temperature for 10–12 h. Aqueous NaHCO$_3$ (100 mL) was then added to the reaction and the layers were separated. The bicarbonate layer was acidified to pH 1 with conc. HCl and extracted with ether (2×100 mL). The organic layers were dried over anhydrous MgSO$_4$, filtered and evaporated under reduced pressure to yield the α-methylene lactones as a mixture of cis- and trans-diastereoisomers as a white solid in overall yields ranging from 58–67%.

The predominant trans-isomer (55–60%) was separated by flash column chromatography using silica gel (ethyl acetate:hexanes:acetic acid 30:70:1). The products were further purified by recrystallization from boiling heaxanes.

Example 1C trans-Tetrahydro-3-methylene-2-oxo-5-n-octyl-4-furancarboxylic acid (C-75)

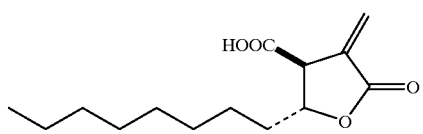

mp 76–77° C. (hexane); IR (film) 3000–3400, 2924, 2852, 1743, 1717, 1660, 1621, 1460 cm$^{-1}$; $^1$H NMR (CDCl$_3$) δ0.84 (t, 3H, J=6.8 Hz), 1.2–1.8 (m, 14H), 3.59 (dt, 1H, J=2.8, 5.6, 12.8 Hz), 4.77 (q, 1H, J=6, 12.8 Hz), 6.0 (d, 1H, J=2.8 Hz), 6.4 (d, 1H, J=3.2 Hz); $^{13}$C NMR (CDCl$_3$) δ14.0, 22.6, 24.7, 29.1, 29.14, 31.7, 35.1, 49.4, 78.7, 125.9, 132.2, 168.1, 174.5; exact mass: calculated=254.1518, found=254.1514.

cis-isomer: mp 74–75.5° C. (hexane); IR (film) 3000–3400, 2922, 2855, 1748, 1713, 1663 cm$^{-1}$; $^1$H NMR (CDCl$_3$) δ0.7 (b, 3H), 1.2–1.8 (b, 14H), 4.0 (dt, 1H, J=2, 7.6

Hz), 4.6 (q, 1H, J=5.6, 7.6 Hz), 5.9 (d, J=2.4 Hz), 6.4 (d, 1H, J=2.0 Hz); $^{13}$C NMR (CDCl$_3$) δ14.0, 22.6, 25.5, 29.1, 29.14, 29.3, 31.3, 31.7, 48.8, 78.0, 125.7, 133.1, 168.8, 174.4.

Example 1D trans-Tetrahydro-3-methylene-2-oxo-5-n-hexyl-4-furancarboxylic acid

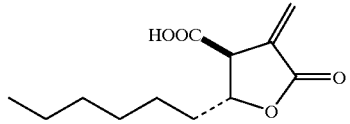

IR (neat) 3000–3400, 2953, 2852, 1743, 1717 1660, 1256, 1460 cm$^{-1}$; $^1$H NMR (CDCl$_3$) δ0.8 (bt, 3H) 1.20–1.81 (m, 10H), 3.59 (dt, 1H, J=2.8, 5.6 Hz), 4.76 (q, 1H, J=6.0, 2.8 Hz), 5.91 (d, 1H, J=2.8 Hz), 6.42 (d, 1H, J=2.8 Hz); $^{13}$C NMR (CDCl$_3$) δ13.9, 22.4, 24.6, 28.7, 31.5, 35.6, 49.4, 78.9, 126.0, 132.2, 168.4, 174.5.

Cis isomer: IR (neat) 3000–3400, 2922, 2855, 1748, 1713, 1663, 1466 cm$^{-1}$; $^1$H NMR (CDCl$_3$) δ0.7 (b, 3H), 1.2–1.8 (b, 10H), 4.0 (bd, 1H, J=7.6 Hz), 4.6 (q, 1H, J=5.6, 7.6 Hz), 5.9 (d, J=2.4 Hz), 6.4 (d, 1H, J=2.4 Hz).

Example 1E trans-Tetrahydro-3-methylene-2-oxo-5-n-heptyl-4-furancarboxylic acid

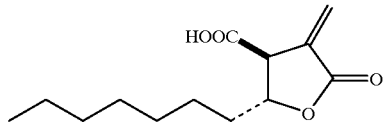

IR (neat) 3000–3400, 2960, 2840, 1747, 1654, 1460 cm$^{-1}$; $^1$H NMR (CDCl$_3$) δ0.7 (b, 3H), 1.3–1.8 (m, 12H), 3.6 (dt, 1H, J=2.8, 5.6 Hz), 4.79 (q, 1H, J=5.6, 12.8 Hz), 6.0 (d, 1H, J=2.4 Hz), 6.45 (d, 1H, J=2.8 Hz).

Example 1F trans-Tetrahydro-3-methylene-2-oxo-5-n-nonyl-4-furancarboxylic acid

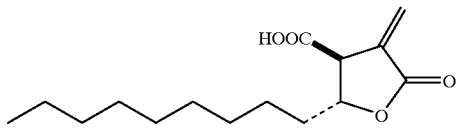

IR (film) 3000–3400, 2924, 2852, 1743, 1717, 1660, 1460 cm$^{-1}$; $^1$H NMR (CDCl$_3$) δ0.84 (t, 3H, J=6.8 Hz), 1.2–1.8 (m, 16H), 3.59 (dt, 1H, J=2.8, 5.6 Hz), 4.77 (q, 1H, J=6, 12.8 Hz), 6.0 (d, 1H, J=2.8 Hz), 6.4 (d, 1H, J=3.2 Hz); $^{13}$C NMR (CDCl$_3$) δ14.1, 22.6, 24.7, 29.1, 29.2, 29.23, 29.3, 29.4, 31.8, 35.7, 49.4, 78.8, 126.0, 132.2, 168.1, 174.7.

Example 1G trans-Tetrahydro-3-methylene-2-oxo-5-n-undecyl-4-furancarboxylic acid

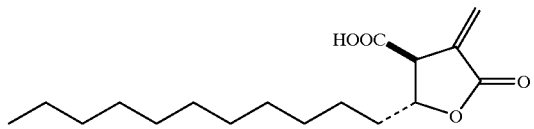

IR (film) 3000–3400, 2924, 2852, 1745, 1717, 1660, 1460 cm$^{-1}$; $^1$H NMR (CDCl$_3$) δ0.84 (t, 3H, J=6.8 Hz), 1.2–1.8 (m, 20H), 3.6 (dt, 1H, J=2.8 Hz, 5.6Hz), 4.77 (q, 1H, J=2.8, 5.6, 12.8 Hz), 6.0 (d, 1H, J=2.8 Hz), 6.4 (d, 1H, J=2.8 Hz); $^{13}$C NMR (CDCl$_3$) δ14.0, 22.6, 24.7, 29.1, 29.19, 29.3, 29.4, 29.47, 29.5, 31.8, 35.7 49.4, 78.8, 126.0, 132.2, 168.3, 174.8.

Example 1H trans-Tetrahydro-3-methylene-2-oxo-5-n-tridecyl-4-furancarboxylic acid

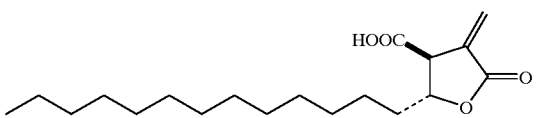

IR (film) 3000–3400, 2919, 2850, 1749, 1719, 1661, 1467 cm$^{-1}$; $^1$H NMR (CDCl$_3$) δ0.84 (t, 3H, J=6.8 Hz), 1.2–1.8 (m, 20H), 3.60 (dt, 1H, J=2.8 Hz, 5.6 Hz), 4.77 (q, 1H, J=5.6, 12.8 Hz), 6.10 (d, 1H, J=2.8 Hz), 6.4 (d, 1H, J=2.8 Hz); $^{13}$C NMR (CDCl$_3$) δ14.0, 22.6, 24.7, 29.1, 29.2, 29.3, 29.38, 29.4, 29.48, 29.5, 29.58, 29.62, 31.8, 35.7, 49.4, 78.8, 125.9, 132.3, 168.3, 174.8.

Example 1I trans-Tetrahydro-3-methylene-2-oxo-5-(3E, 6E-octadieny)-4-furancarboxylic acid

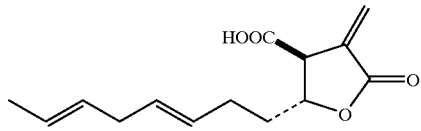

IR (neat) 3000–3400, 2924, 1743, 1717, 1660, 1610, 1465 cm$^{-1}$; $^1$H NMR (CDCl$_3$) d 1.61 (d, 3H), 1.70–2.25 (m, 4H), 2.65 (m, 2H), 3.61 (dt, 1H, J=2.8, 5.6 Hz), 4.80 (q, 1H, J=5.5, 12.6 Hz), 5.2–5.4 (m, 4H), 6.05 (d, 1H, J=2.8 Hz), 6.38 (d, 1H, J o=2.8 Hz).

Example 1J trans-Tetrahydro-3-methylene2-oxo-5-(3E-4-(3-fluorophenyl))but-3-enyl-4-furancarboxylic acid

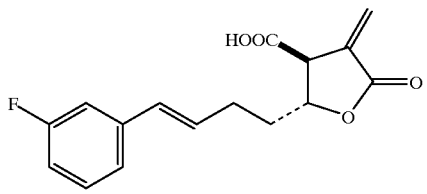

IR (neat) 3000–3400, 2917, 2877, 1749, 1717, 1660, 1500 cm$^{-1}$; $^1$H NMR (CDCl$_3$) δ1.80–2.65 (m, 2H), 3.60 (dt, 1H, J=2.8, 5.6 Hz), 4.80 (q, 1H, J=5.5, 12.6 Hz), 6.04–6.42 (m, 4H), 6.75–7.38 (m, 4H).

Example 2

Cerulenin Induces Weight Loss in Athymic Nude Mice

Athymic mice received 60 mg/kg cerulenin i.p. in 25% DMSO/saline or vehicle alone each day for 1 week. The animal weights were recorded every two days up to day 15. Average animal weight for both groups of mice is plotted against treatment day in FIG. 1. Error bars represent standard error of the mean. Intraperitoneal administration of cerulenin for seven days to nude mice resulted in an average 28% loss of weight by day eight, with mice returning to 96% of their original weight by day 14 (FIG. 1). In addition there was a 28% reduction of feces mass in the cerulenin-treated group consistent with deceased food intake. Water intake was not appreciable altered. Observation of the mice showed normal activity even during the period of maximal weight loss.

Necropsy of treated animals from a parallel experiment showed markedly decreased subcutaneous fat and abdominal fat deposits, and reduced liver volume consistent with reduction in hepatic fat accumulation. Microscopically, the liver was unremarkable without necrosis or inflammation but cerulenin-treated animals had an absence of the fat droplets which were seen in controls. In addition, white fat deposits around abdominal organs were significantly reduced, but brown fat deposits remained. While the white fat deposits were reduced, no decrease in muscle mass was detected histologically.

Example 3

Cerulenin Induces Weight Loss in Nude Mice OVCAR-3 Xenografts

Figure 2:
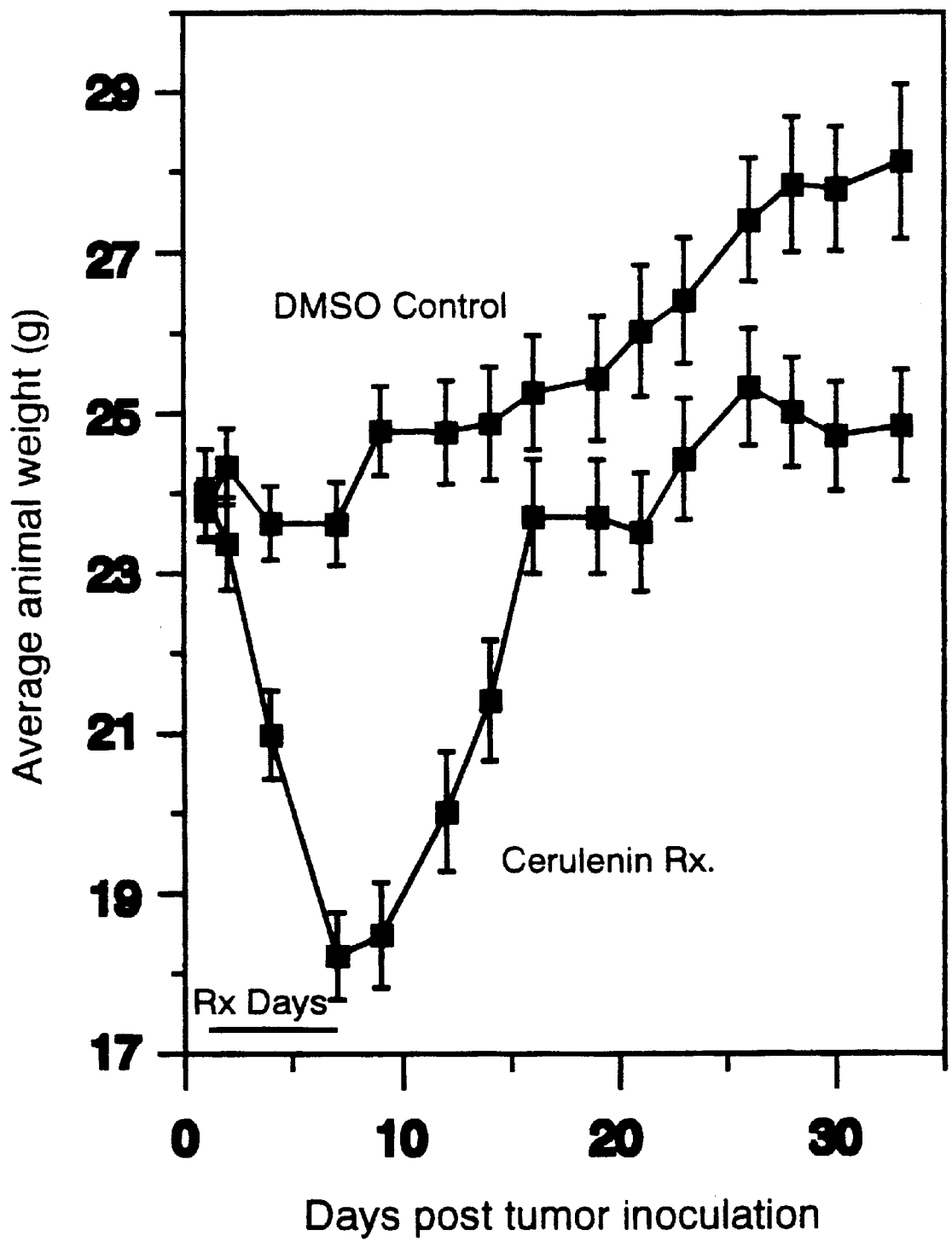
FIG. 2 shows cerulenin-induced weight loss in nude mice inoculated with OVCAR-3 cells.

Cerulenin was administered as described in Example 2 above to mice which received 10$^7$ OVCAR-3 human ovarian cancer cells. Athymic mice received 0.1 ml of packed NIH-OVCAR-3 cells (approximately 10$^5$ cells) intraperitoneally on treatment day 0. Beginning on day 1, treated mice received 80 mg/kg cerulenin i.p. in 25% DMSO/saline for 1 week, while untreated mice received vehicle alone. As shown in FIG. 2, cerulenin-treated mice experienced a mean weight loss of 25% of original body mass during the treatment period. Weight loss constitutes the major toxicity observed during fatty acid synthesis inhibition therapy with cerlenin; the mice regained inception body mass within 10 days following treatment. Importantly, urinalysis failed to demonstrate any diabetogenic effect of cerulenin.

Example 4

Cerulenin Inhibits Fatty Acid Synthesis in vivo

Fatty acid synthesis was measured using metabolic labeling in vivo with [U-$^3$H]-acetate as described in Pizer, et al., 1996, Cancer Res., 56:1189–1193. OVCAR-3 ascites tumor fatty acid synthesis was reduced by 43%, after intraperitoneal administration of cerulenin performed as in Example 3, demonstrating that cerulenin inhibits fatty acid synthesis in vivo. No augmentation of inhibition was achieved with high dose cerulenin [6 mg/mouse] over the standard dose [2 mg/mouse], indicating that drug activity was probably maximal. There was no effect on mean hepatic fatty acid synthesis after cerulenin due to the short half life (<15 min.) of the drug in ascites.

In parallel experiments using mice without tumor, inhibition of fatty acid synthesis in the range of 50% was observed in liver. Thus, the reversible cerulenin-induced weight loss may be the result of fatty acid synthesis inhibition as well as decreased appetite in the mice.

Example 5

C-75 Inhibition of Fatty Acid Synthesis

Incubation of C-75 (50 μg/ml) with a hypotonic lysate (20 mM K$_2$PO$_4$ pH 6.6 at 25° C.) of OVCAR-3 ascites cells at 37° C. for 180 min results in a 3-fold reduction of FAS activity compared to control lysate (5.6 nM NADPH oxidized/min by control; 1.8 with C-75) as measured by monitoring the malonyl-CoA dependent oxidation of NADPH at 340 nm U.V. Incubation at 4° abolishes the inhibitory effect of C-75 while not affecting the activity of the controls. While relatively high concentrations of C-75 were required in the lysate to achieve inhibition of FAS; in a living cell, the effect of C-75 may be more efficient, requiring lower concentrations of compound.

Figure 3:
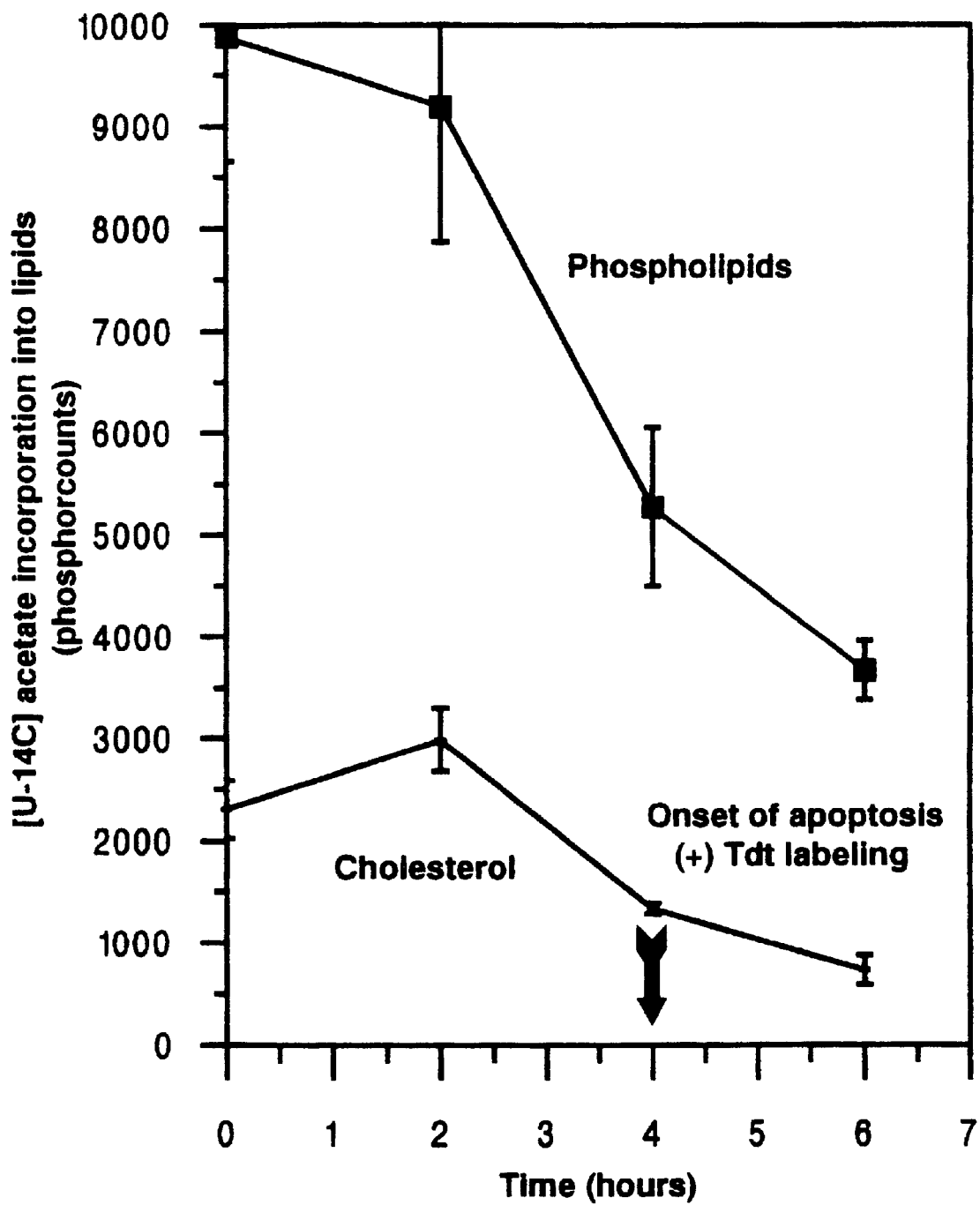
FIG. 3 shows C-75 inhibition of acetate incorporation into acylglycerides by HL60 cells.

In vitro studies in HL60 human promyelocytic leukemia cells demonstrated that C-75 inhibits fatty add synthesis. HL60 cells were labeled with [U$^{14}$C]-acetate in the presence of 10 μg/ml C-75; cells were incubated in 5% CO$_2$ at 37° C. Results are plotted in FIG. 3; each time point was performed in triplicate, error bars are the standard deviation. FIG. 3 shows a time dependent reduction of label incorporation into phospholipids, representing nearly a three-fold reduction in fatty acid synthesis. Pilot in vivo metabolic labeling studies have demonstrated that C-75 reduces [U-$^3$H] acetate incorporation into fatty acids in mouse liver by 30%.

Example 6

C-75 Induces Weight Loss in vivo

Figure 4:
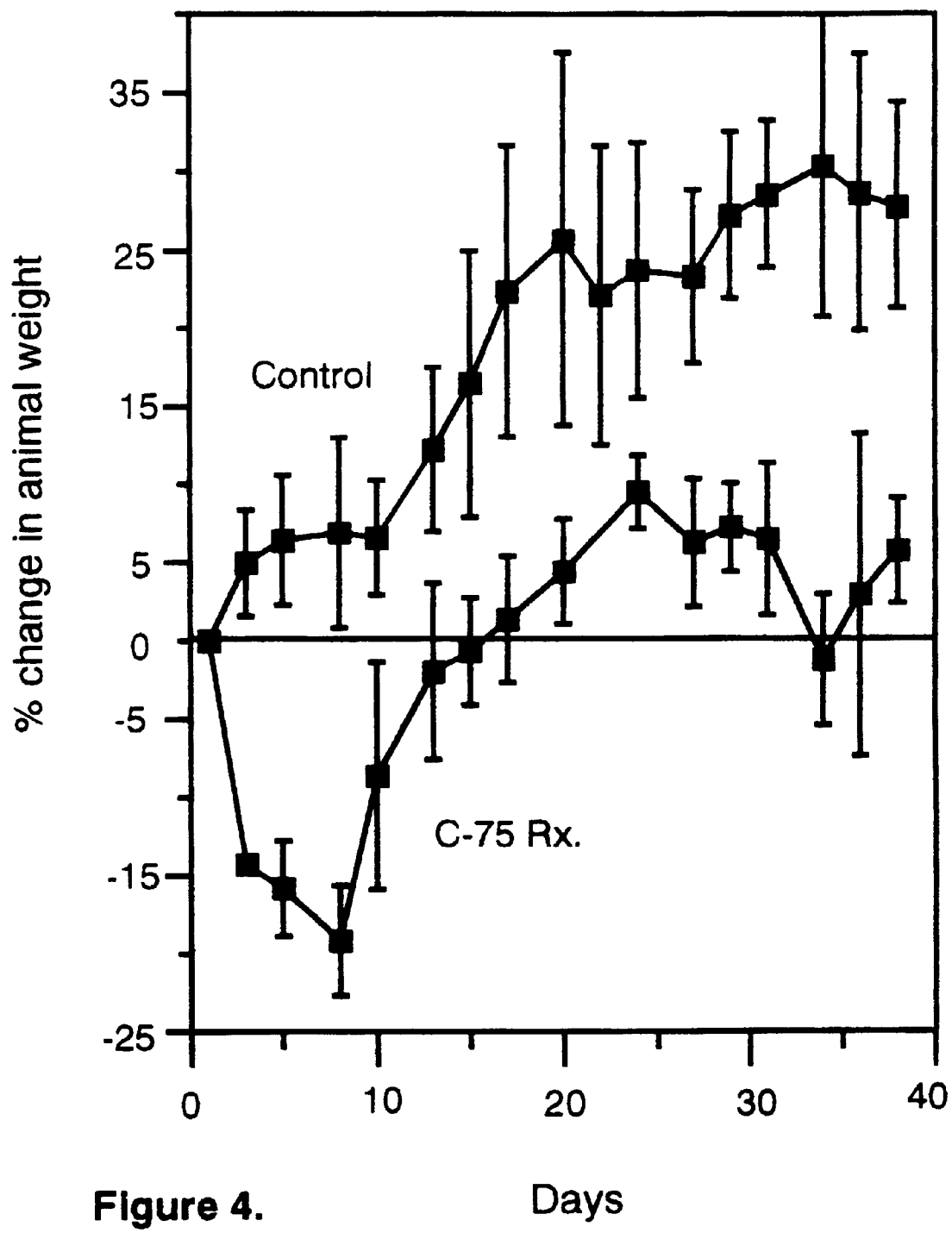
FIG. 4 shows C-75-induced weight loss in nude mice inoculated with OVCAR-3 cells and monitored for 40 days.

C-75 was tested in vivo in a pilot study against the OVCAR-3 xenograft model of Example 4. Ten mice were inoculated intraperitoneally with 10$^7$ OVCAR-3 cells. The mice were treated on days 1, 3, and 5 with either DMSO or 60 mg/kg C-75. Results are plotted in FIG. 4. C-75 treated mice experienced a 20% reduction in weight loss by day eight. Animals regained their original weight by day 15, increased their weight to nearly 110% of original body weight by day 24, and achieved original body weight by day 34.

Example 7

C-75 Inhibition of Fatty Acid Synthesis by HL60 Cells

Figure 5:
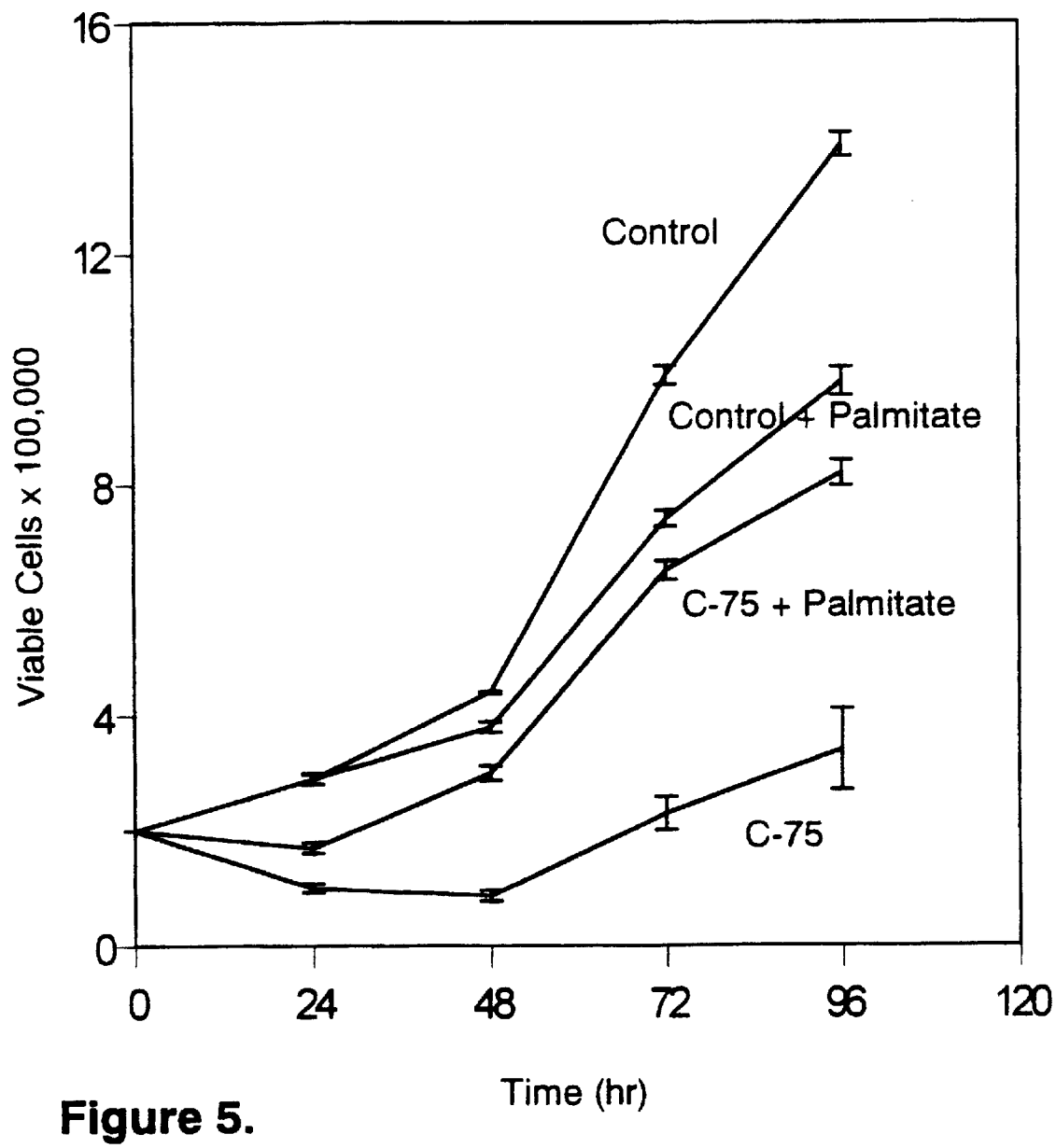
FIG. 5 shows rescue of HL60 cells from C-75 inhibition by exogenous fatty acid.

In vitro studies in HL60 human promyelocytic leukemia cells demonstrate that C-75 inhibition of fatty add synthesis can be reversed by exogenous fatty acid addition. 200,000 HL60 cells were plated in 24- well plates in 1 ml fatty acid free medium with or without palmitate (80 micromolar, complexed to fatty acid free albumin 0.2:1). Cells were treated with 2.5 µg/ml of C-75. Cells were incubated in 5% $CO_2$ at 37° C. and viable cells were counted with trypan blue exclusion at 24, 28, 72, and 96 hours. Results are plotted in FIG. 5; each time point was performed in triplicate, error bars are the standard deviation. FIG. 5 shows that palmitate rescues HL60 cells from C-75. Note that palmitate alone causes some suppression of HL60 proliferation.

Example 8

Figure 6:
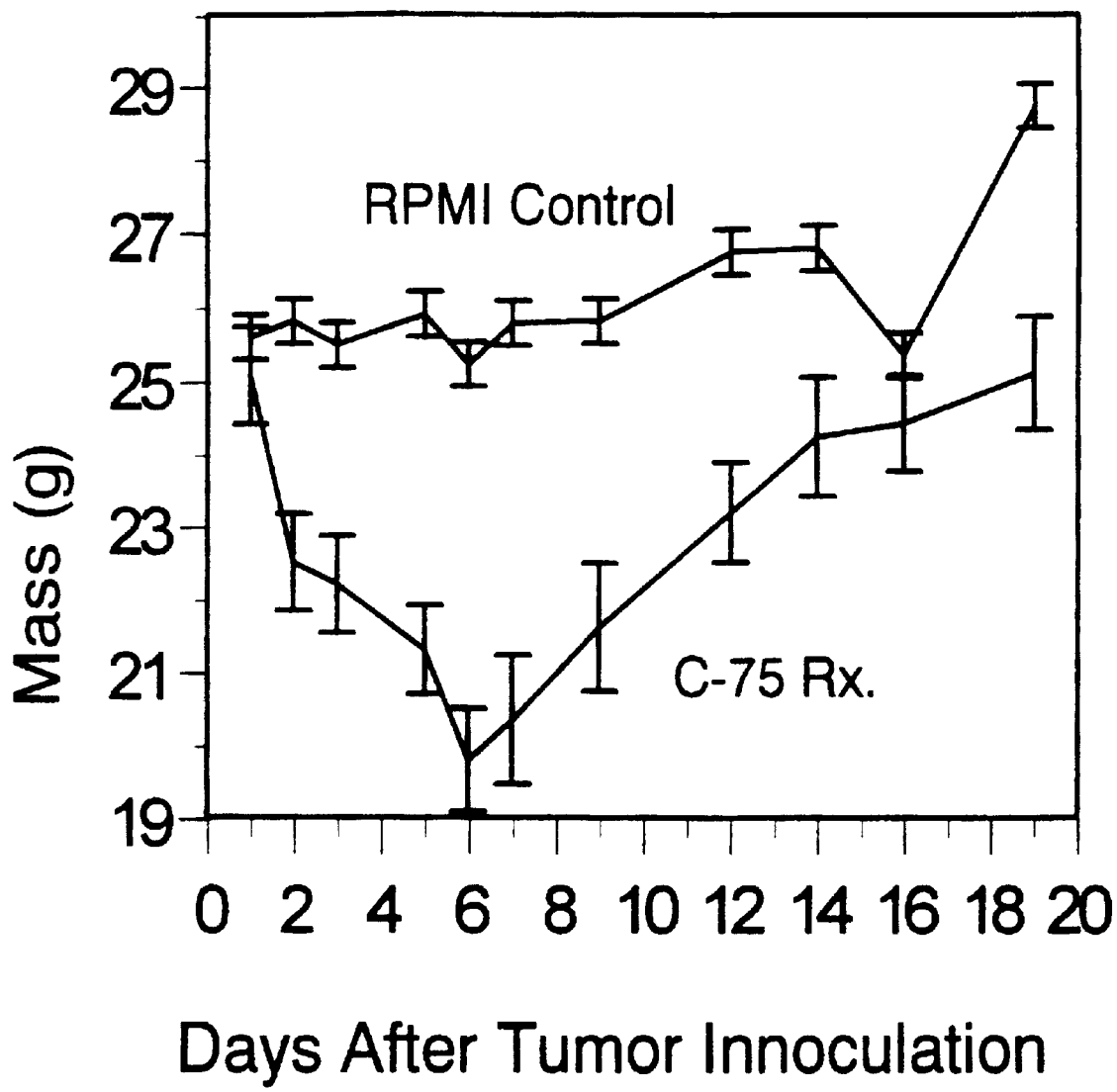
FIG. 6 shows C-75-induced weight loss in nude mice inoculated with OVCAR-3 cells and monitored for 19 days.
Figure 7:
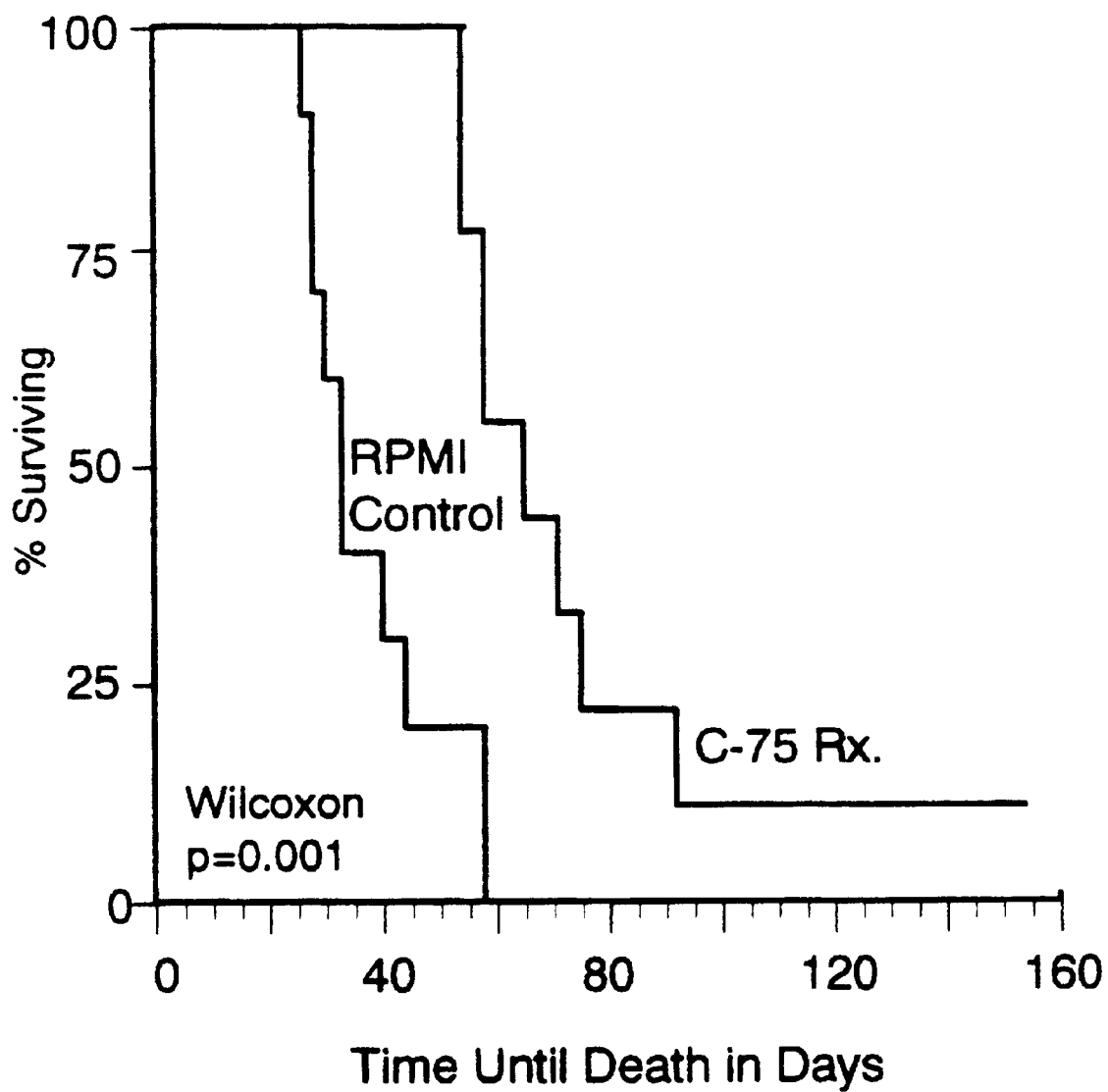
FIG. 7 shows Kaplan-Meier Survival Curves for nude mice inoculated with OVCAR-3 cells with or without C-75 treatment.
Figure 8:
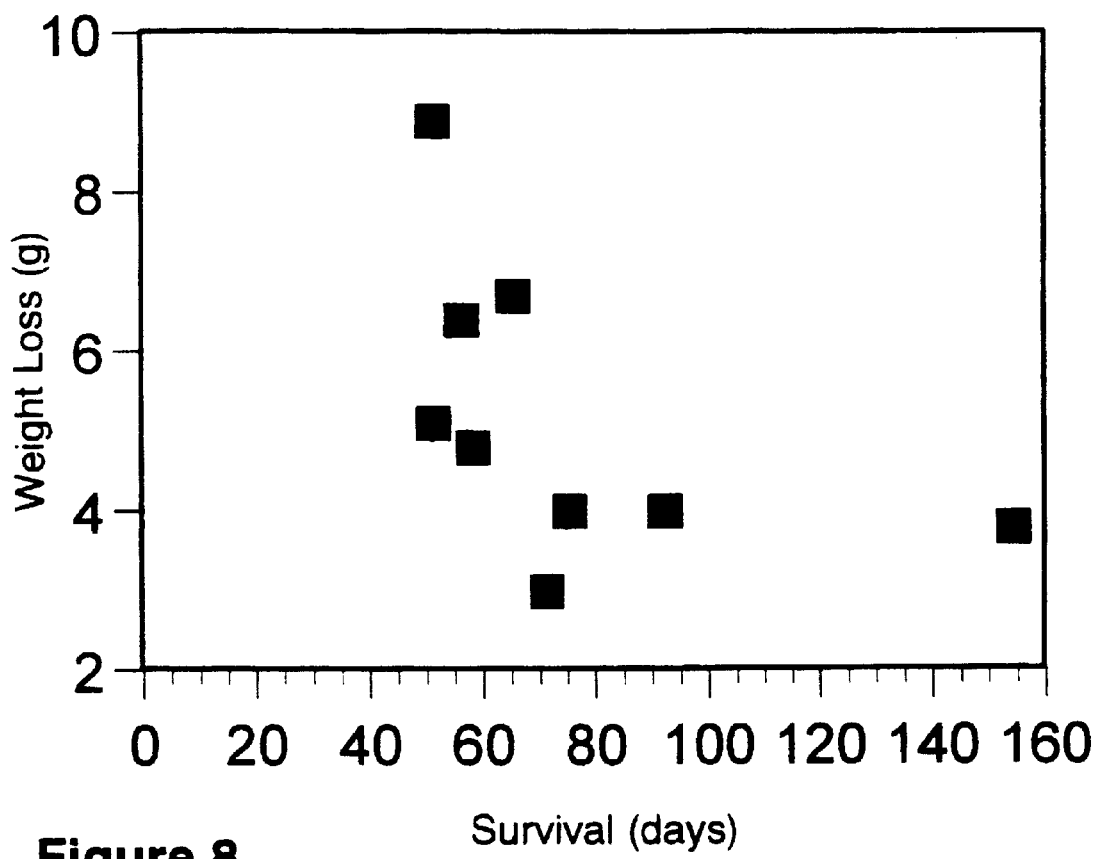
FIG. 8 shows maximum weight loss vs. survival for individual mice.

C-75 Induces Weight Loss in vivo 20 nude mice (Harland) mice were inoculated on Day 0 with 0.1 ml packed OVCAR-3 cells. 10 mice received transisomer of C-75 (20 mg/kg) in 100 ul RPMI on days 1, 3, and 5. 10 mice received 100 ul of RPMI i.p. alone on days 1, 3, and 5. Animals were weighed on days indicated on FIG. 6. Animals were sacrificed when 30% increase in body weight occurred from tumor growth. C-75 causes weight loss in mice as shown in FIG. 6. As shown in the Survival Curve in FIG. 7, C-75 causes increased survival of the xenograft (p=0.001 Wilcoxon and Mantel Life Table Statistics.) FIG. 8 is a plot of maximum weight loss vs. survival for individual mice, and this plot demonstrates that there is no correlation between survival and amount of weight loss for individual mice.

Example 9

Dose Response for C-75

Figure 9:
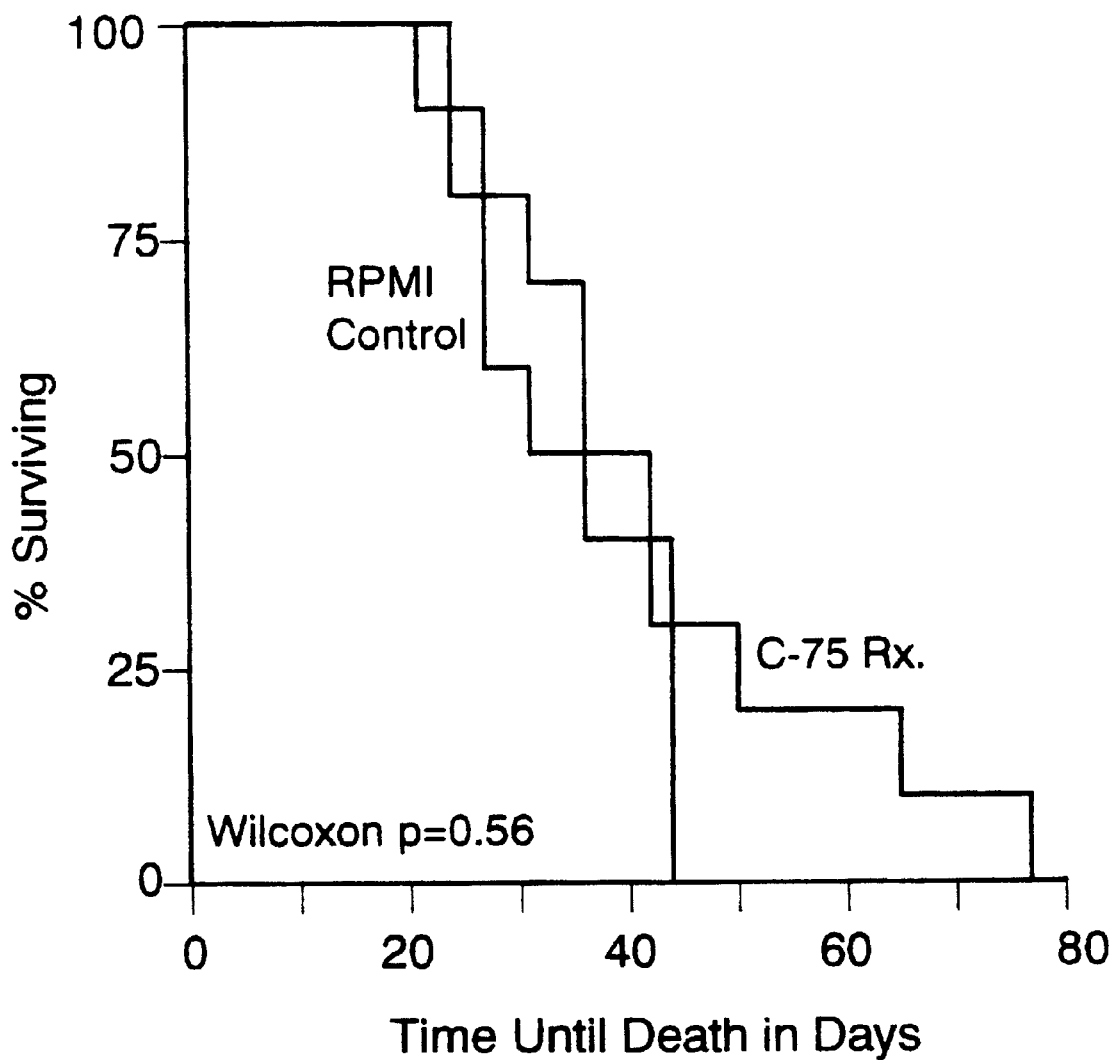
FIG. 9 shows Kaplan-Meier Survival Curves for nude mice inoculated with OVCAR-3 cells with or without a single C-75 treatment.

FIG. 9 shows the results for an experiment performed as described for Example 8, except only one dose of C-75 was given. Survival is plotted on FIG. 9, and there is a trend showing increased survival, but it was not statistically significant (wilcoxon p=0.56, Mantel p=0.52). This indicates a dose response to the anti-tumor effect of C-75. These mice showed an average maximum weight loss of about 3 grams on day 3.

We claim:

1. A method for inducing weight loss in an animal comprising administering to the animal a compound which reduces fatty acid synthase (FAS) activity in adipocytes or liver cells, wherein said compound is not a fat or a metabolizable product thereof.

2. A method for treating a condition responsive to reduction in adipose tissue mass in an animal comprising administering to the animal a composition which reduces fatty acid synthase (FAS) activity in adipocytes or liver cells, wherein said composition does not contain a fatty acid or fatty acid residue.

3. The method according to claim 2, wherein the condition is obesity or non-insulin dependent diabetes mellitus.

4. The method according to claim 1 or 2, wherein the composition consists essentially of an inhibitor of FAS.

5. The method according to claim 1 or 2, wherein the composition inhibits biosynthesis of FAS.

6. The method according to claim 1 or 2, wherein the composition is administered in an amount sufficient to reduce adipocyte mass in the animal.

7. The method according to claim 1 or 2, wherein the composition is administered in an amount sufficient to reduce FAS activity in liver cells of the animal.

8. A method for inducing weight loss in an animal comprising administering to the animal an inhibitor of fatty acid synthase (FAS).

9. The method of claim 8, wherein the inhibitor of FAS is administered in an amount sufficient to reduce fatty acid synthesis in adipose tissue or liver.

10. A pharmaceutical composition comprising a 5-substituted 2-oxo-3-methylene-4-furancarboxylic acid, wherein the substituent is selected from:

(a) a saturated linear alkyl group of 3–18 carbons;

(b) a saturated branched alkyl group of 3–18 carbons;

(c) an unsaturated linear or branched alkyl group of 3–18 carbons;

(d) 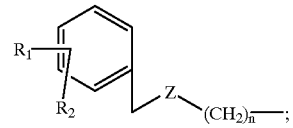

(e) 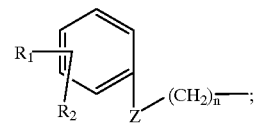

(f) 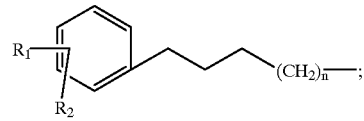

(g) 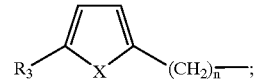

(h) 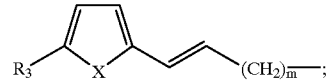

(i) 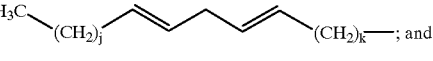

(j) 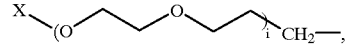

wherein R1 and R2 each are H, $CH_3$, $C_2H_5$, $C_3H_7$, $C_4H_9$, $CF_3$, $OCH_3$, F, Cl, or Br; R3 is H, $CH_3$, $C_2H_5$, $C_3H_7$, $C_4H_9$, COOH, $COOCH_3$, $COOC_2H_5$, $COOC_3H_7$, or $COOC_4H_9$; R4 is H, $CH_3$, $C_2H_5$, $C_3H_7$, $C_4H_9$; X is N, S or O; Z is $CH_2$, O, NH or S; i is 1 to 5; j is 0 to 10; k is 1 to 10; m is 1–13; and n is 1 to 15, and R1 and R2 may be the same or different.

11. The composition of claim 10, wherein the substituent is $C_4H_9$, $C_5H_{11}$, $C_6H_{13}$, $C_7H_{15}$, $C_8H_{17}$, $C_9H_{19}$, $C_{10}H_{21}$, $C_{12}H_{25}$, $C_{14}H_{29}$, $C_{15}H_{31}$, $C_{16}H_{33}$, $C_{17}H_{35}$, or $C_{18}H_{37}$.

12. The composition of claim 10, wherein the substituent is n-octyl.

13. The composition of claim 10 wherein the substitutent is 3E-4-(3-fluorophenyl)but-3-enyl or 3E,6E-octadienyl.

14. A method for inducing weight loss in an animal comprising administering to the animal the composition of claim 10.

15. A method of inhibiting growth of tumor cells in an animal, said cells expressing at least one enzyme of the fatty acid biosynthetic pathway, comprising administering the composition of claim 10 to the tumor cells.

16. The method of claim 15, wherein said cells express fatty acid synthase (FAS).

17. The method of claim 15, wherein the composition is administered in an amount specifically cytotoxic to said tumor cells.

18. The use of a 5-substituted 2-oxo-3-methylene-4-furancarboxylic acid according to claim 10 to prepare a composition for treatment of a condition responsive to reduction in adipose tissue mass in an animal or for treatment to induce weight loss in an animal.

19. The use of an inhibitor of FAS to prepare a composition for treatment of a condition responsive to reduction in adipose tissue mass in an animal or for treatment to induce weight loss in an animal.

* * * * *